(12) United States Patent
Kaplan

(10) Patent No.: US 9,790,267 B2
(45) Date of Patent: Oct. 17, 2017

(54) GLYPICAN-3-SPECIFIC ANTIBODY AND USES THEREOF

(71) Applicants: The Trustees of the University of Pennsylvania, Philadelphia, PA (US); The United States of America, as represented by the Secretary of the Department of Veterans Affairs, Washington, DC (US)

(72) Inventor: David Kaplan, Media, PA (US)

(73) Assignees: The Trustees of the University of Pennsylvania, Philadelphia, PA (US); The United States of America, as represented by the Secretary of the Department of Veterans Affairs, Washington, DC (US)

( * ) Notice: Subject to any disclaimer, the term of this patent is extended or adjusted under 35 U.S.C. 154(b) by 125 days.

(21) Appl. No.: 14/181,870

(22) Filed: Feb. 17, 2014

(65) Prior Publication Data

US 2014/0170114 A1 Jun. 19, 2014

Related U.S. Application Data

(63) Continuation of application No. PCT/US2012/062765, filed on Oct. 31, 2012.

(60) Provisional application No. 61/557,174, filed on Nov. 8, 2011.

(51) Int. Cl.

| | |
|---|---|
| *C07K 16/30* | (2006.01) |
| *C12N 15/13* | (2006.01) |
| *C07K 16/18* | (2006.01) |
| *G01N 33/574* | (2006.01) |
| *C07K 14/705* | (2006.01) |
| *C07K 16/28* | (2006.01) |

(52) U.S. Cl.
CPC ........ *C07K 16/18* (2013.01); *C07K 14/70521* (2013.01); *C07K 16/2809* (2013.01); *C07K 16/30* (2013.01); *C07K 16/303* (2013.01); *G01N 33/57438* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,694,778 A | 9/1987 | Learn et al. |
| 4,716,111 A | 12/1987 | Osband et al. |
| 4,816,567 A | 3/1989 | Cabilly et al. |
| 5,199,942 A | 4/1993 | Gillis |
| 5,225,539 A | 7/1993 | Winter |
| 5,229,275 A | 7/1993 | Goroff |
| 5,350,674 A | 9/1994 | Boenisch |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,585,089 A | 12/1996 | Queen et al. |
| 5,585,362 A | 12/1996 | Wilson et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,766,886 A | 6/1998 | Studnicka et al. |
| 5,814,318 A | 9/1998 | Lonberg et al. |
| 5,858,358 A | 1/1999 | June et al. |
| 5,883,223 A | 3/1999 | Gray |
| 5,939,598 A | 8/1999 | Kucherlapati et al. |
| 6,120,766 A | 9/2000 | Hale et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,410,319 B1 | 6/2002 | Raubitschek et al. |
| 6,534,055 B1 | 3/2003 | June et al. |
| 6,548,640 B1 | 4/2003 | Winter |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |

(Continued)

FOREIGN PATENT DOCUMENTS

| | | |
|---|---|---|
| EP | 239400 | 3/1987 |
| EP | 592106 | 11/2004 |

(Continued)

OTHER PUBLICATIONS

Paul, Fundamental Immunology, 3rd Edition, 1993, pp. 292-295.*
Rudikoff et al. (Proceedings of the National Academy of Sciences USA, vol. 79, p. 1979-1983, 1982).*
Kaplan (Hepatology, vol. 59, Supplement 1, p. 1279a, Abstract 1951, 2011).*
Feldhaus (Nature Biotechnology, vol. 21, p. 163-170, 2003).*
Bork, "Powers and pitfalls in sequence analysis: the 70% hurdle", Genome Res. 10(4), Apr. 2000, 398-400.

(Continued)

*Primary Examiner* — Michael D Allen
(74) *Attorney, Agent, or Firm* — Saul Ewing LLP; Kathryn Doyle

(57) ABSTRACT

The present invention relates to compositions and methods for diagnosing and treating diseases, disorders or conditions associated with dysregulated expression of GPC3. The invention provides novel antibodies that specifically bind to glypican-3 (GPC3). The invention also relates to a fully human chimeric antigen receptor (CAR) wherein the CAR is able to target GPC3.

4 Claims, 17 Drawing Sheets

(56) References Cited

U.S. PATENT DOCUMENTS

| | | | |
|---|---|---|---|
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 2004/0101519 | A1 | 5/2004 | June et al. |
| 2005/0042664 | A1 | 2/2005 | Wu et al. |
| 2005/0048617 | A1 | 3/2005 | Wu et al. |
| 2005/0282252 | A1 | 12/2005 | Siegel |
| 2006/0014223 | A1 | 1/2006 | Aburatani et al. |
| 2006/0034810 | A1 | 2/2006 | Riley et al. |
| 2006/0121005 | A1 | 6/2006 | Berenson et al. |
| 2007/0190599 | A1 | 8/2007 | Nakano et al. |
| 2007/0217997 | A1 | 9/2007 | Devy et al. |
| 2008/0138827 | A1 | 6/2008 | Watanabe et al. |
| 2010/0209432 | A1 | 8/2010 | Terrette et al. |
| 2011/0076275 | A1 | 3/2011 | Igawa et al. |
| 2012/0135525 | A1* | 5/2012 | Brown .................. C12N 5/0696 435/455 |
| 2014/0044714 | A1 | 2/2014 | Ho et al. |

FOREIGN PATENT DOCUMENTS

| | | |
|---|---|---|
| EP | 519596 | 2/2005 |
| WO | WO91/09967 | 7/1991 |
| WO | WO91/10741 | 7/1991 |
| WO | WO93/17105 | 9/1993 |
| WO | WO96/33735 | 10/1996 |
| WO | WO96/34096 | 10/1996 |
| WO | WO98/16654 | 4/1998 |
| WO | WO98/24893 | 6/1998 |
| WO | WO98/46645 | 10/1998 |
| WO | WO98/50433 | 11/1998 |
| WO | WO01/29058 | 4/2001 |
| WO | WO01/96584 | 12/2001 |

OTHER PUBLICATIONS

Bowie, et al., "Deciphering the message in protein sequences: tolerance to amino acid substitutions", Science 247, Mar. 16, 1990, 1306-1310.

Burgess, et al., "Possible dissociation of the heparin-binding and mitogenic activities of heparin-binding (acidic fibroblast) growth factor-1 from its receptor-binding activities by site-directed mutagenesis of a single lysine residue", J Cell Biol 111, Nov. 1990, 2129-2138.

Lazar, et al., "Transforming growth factor alpha: mutation of aspartic acid 47 and leucine 48 results in different biological activities", Mol Cell Biol. 8(3), Mar. 1988, 1247-1252.

Abdul-Al et al., "Glypican-3 expression in benign liver tissue with active hepatitis C: implications for the diagnosis of hepatocellular carcinoma." 2008 Hum Pathol 39(2): 209-212.

Aburatani, "Discovery of a new biomarker for gastroenterological cancers." 2005, J Gastroenterol 40, S16:1-6.

Anatelli, et al., "Value of glypican 3 immunostaining in the diagnosis of hepatocellular carcinoma on needle biopsy." 2008, Am J Clin Path 130:219-223.

Baca et al., "Antibody humanization using monovalent phage display." J. Biol. Chem., 272(16):10678-84 (1997).

Barkholt et al., "Safety analysis of ex vivo-expanded NK and NK-like T cells administered to cancer patients: a phase I clinical study." 2009 Immunotherapy 1(5): 753-764.

Baumhoer et al., "Glypican 3 expression in human nonneoplastic, preneoplastic, and neoplastic tissues: a tissue microarray analysis of 4,387 tissue samples." 2008 Am J Clin Pathol 129(6): 899-906.

Berg et al., "Selective expansion of a peripheral blood CD8+ memory T cell subset expressing both granzyme B and L-selectin during primary viral infection in renal allograft recipients." 1998, Transplant Proc. 30(8):3975-3977.

Bird et al., "Single-chain antigen-binding proteins." 1988, Science 242:423-426.

Bruggermann et al., "Designer mice: the production of human antibody repertoires in transgenic animals." 1993, Year in Immunol., 7:33.

Caldas et al., "Design and synthesis of germline-based hemi-humanized single-chain Fv against the CD18 surface antigen." 2000, Protein Eng., 13(5):353-60.

Capurro et al., "Glypican-3: a novel serum and histochemical marker for hepatocellular carcinoma." 2003 Gastroenterology 125(1): 89-97.

Capurro, et al., "Glypican-3 as a serum marker for hepatocellular carcinoma." 2005, Cancer Res 65:372.

Carpenito, et al., "Control of large, established tumor xenografts with genetically retargeted human T cells containing CD28 and CD137 domains." 2009, Proc Natl Acad Sci U S A 106:3360-3365.

Carter et al.,"Humanization of an anti-p185HER2 antibody for human cancer therapy." Proc. Natl. Acad. Sci. USA, 89:4285 (1992).

Chothia et al., "Canonical structures for the hypervariable regions of immunoglobulins." J. Mol. Biol., 196:901-917 (1987).

Clackson et al., "Making antibody fragments using phage display libraries." Nature, 352:624-628 (1991).

Coston, et al., "Distinction of hepatocellular carcinoma from benign hepatic mimickers using Glypican-3 and CD34 immunohistochemistry." 2008, Am J Surg Pathol 32:433-444.

Couto et al., "Designing human consensus antibodies with minimal positional templates." 1995, Cancer Res., 55 (23 Supp):5973s-5977s.

Couto et al., "Anti-BA46 monoclonal antibody Mc3: humanization using a novel positional consensus and in vivo and in vitro characterization." 1995, Cancer Res., 55(8):1717-22.

Duchosal et al., "Immunization of hu-PBL-SCID mice and the rescue of human monoclonal Fab fragments through combinatorial libraries." 1992, Nature, 355:258-262.

El-Serag, "Hepatocellular carcinoma: an epidemiologic view." 2002, J Clin Gastroenterology 35:S72-78.

Feng et al., "Recombinant soluble glypican 3 protein inhibits the growth of hepatocellular carcinoma in vitro." 2011 Int J cancer J Int du cancer 128(9): 2246-2247.

Filmus et al., "Glypican-3 and alphafetoprotein as diagnostic tests for hepatocellular carcinoma." 2004, Mol Diagn 8(4): 207-212.

Garland et al., "The use of Teflon cell culture bags to expand functionally active CD8+ cytotoxic T lymphocytes." 1999, J. Immunol Meth. 227(1-2):53-63.

Genbank/NCBI accession No. NM004484, deposited on Sep. 9, 2009.

Greten et al. "A phase II open label trial evaluating safety and efficacy of a telomerase peptide vaccination in patients with advanced hepatocellular carcinoma." 2010, BMC Cancer 10: 209 (7 pages).

Griffith et al., "Human anti-self antibodies with high specificity from phage display libraries." 1993, EMBO J., 12:725-734.

Haanen et al., "Selective expansion of cross-reactive CD8(+) memory T cells by viral variants." 1999, J. Exp. Med. 190(9):1319-1328.

Hippo et al., "Identification of soluble NH2-terminal fragment of glypican-3 as a serological marker for early-stage hepatocellular carcinoma." 2004, Cancer Res 64:2418-2423.

Huston et al. "Protein engineering of antibody binding sites: recovery of specific activity in an anti-digoxin single-chain Fv analogue produced in *Escherichia coli*." 1988, Proc. Natl. Acad. Sci. USA 85:5879-5883.

Jakobovits et al., "Germ-line transmission and expression of a human-derived yeast artificial chromosome." 1993, Nature, 362:255-258.

Jakobovits et al., "Analysis of homozygous mutant chimeric mice: deletion of the immunoglobulin heavy-chain joining region blocks B-cell development and antibody production," 1993, Proc. Natl. Acad. Sci. USA, 90:2551-5.

Jones et al., "Replacing the complementarity-determining regions in a human antibody with those from a mouse." 1986, Nature, 321: 522-525.

Korangy et al., "Immunotherapy of hepatocellular carcinoma." 2010 Expert Rev Gastroenterol Hepatol 4(3):345-353.

(56) References Cited

OTHER PUBLICATIONS

Levrero, et al., "Control of cccDNA function in hepatitis B virus infection." 2009, J Hepatol 51:581-592.
Lonberg and Huszar, Human antibodies from transgenic mice. 1995, Int. Rev. Immunol., 13:65-93.
Marks et al., "By-passing immunization. Human antibodies from V-gene libraries displayed on phage." 1991, J. Mol. Biol., 222:581-597.
McCafferty et al., "Phage antibodies: filamentous phage displaying antibody variable domains" 1990, Nature, 348:552-554.
Midorikawa et al., "Glypican-3, overexpressed in hepatocellular carcinoma, modulates FGF2 and BMP-7 signaling." 2003, Int J Cancer 103(4):455-465.
Morea et al., "Antibody modeling: implications for engineering and design." 2000, Methods, 20(3):267-79.
Nakano, et al., "Generation of a humanized anti-glypican 3 antibody by CDR grafting and stability optimization." 2010, Anticancer Drugs 21:907-916.
Nakatsura et al., "Glypican-3, overexpressed specifically in human hepatocellular carcinoma, is a novel tumor marker." 2003, Biochem Biophys Res Commun 306(1): 16-25.
Padlan, "A possible procedure for reducing the immunogenicity of antibody variable domains while preserving their ligand-binding properties." 1991, Molecular Immunology, 28(4/5):489-498.
Palmer et al., "A phase II study of adoptive immunotherapy using dendritic cells pulsed with tumor lysate in patients with hepatocellular carcinoma." 2009 Hepatology 49(1): 124-132.
Pedersen et al., "Comparison of surface accessible residues in human and murine immunoglobulin Fv domains. Implication for humanization of murine antibodies." 1994, J. Mol. Biol., 235(3):959-73.
Presta et al., "Humanization of an antibody directed against IgE." 1993, J. Immunol., 151:2623-32.
Presta, "Antibody engineering." 1992, Curr. Op. Struct. Biol., 2(4):593-598.
Reichmann et al., "Reshaping human antibodies for therapy." 1988, Nature, 332:323-329.
Roder et al., "The EBV-hybridoma technique." 1986, Methods Enzymol., 121:140-167.
Roguska et al., "Humanization of murine monoclonal antibodies through variable domain resurfacing." 1994, PNAS, 91:969-973.
Roguska et al., "A comparison of two murine monoclonal antibodies humanized by CDR-grafting and variable domain resurfacing." 1996, Protein Eng., 9(10):895-904.
Rosenberg et al., "Use of tumor-infiltrating lymphocytes and interleukin-2 in the immunotherapy of patients with metastatic melanoma. A preliminary report." 1988, New Eng. J. of Med. 319:1676-80.
Ruan et al., "Inhibition of glypican-3 expression via RNA interference influences the growth and invasive ability of the MHCC97-H human hepatocellular carcinoma cell line." 2011, Int J Mol Med 28(4):497-503.
Sandhu J S, "A rapid procedure for the humanization of monoclonal antibodies." 1994, Gene, 150(2):409-10.
Scholler et al., "Method for generation of in vivo biotinylated recombinant antibodies by yeast mating." 2006, J Immunol Methods 317(1-2):132-143.
Shaker, et al., "Detection of myxovirus resistance protein A in lichen planus lesions and its relationship to hepatitis C virus." 2009, Br J Dermatol 160:980-983.
Sims et al., "A humanized CD18 antibody can block function without cell destruction." 1993, J. Immunol., 151:2296-308.
Skerra et al., "Assembly of a functional immunoglobulin Fv fragment in *Escherichia coli*." 1988, Science 242:1038-1041.
Studnicka et al., "Human-engineered monoclonal antibodies retain full specific binding activity by preserving non-CDR complementarity-modulating residues." 1994, Protein Engineering, 7(6):805-814.
Sun et al., "Suppression of glypican 3 inhibits growth of hepatocellular carcinoma cells through up-regulation of TGF-β2." 2011, Neoplasia 13(8): 735-747.
Sung et al., "Glypican-3 is overexpressed in human hepatocellular carcinoma." 2003, Cancer Sci 94(3): 259-262.
Takai et al., "Histopathological analyses of the antitumor activity of anti-glypican-3 antibody (GC33) in human liver cancer xenograft models: The contribution of macrophages." 2009, Cancer Biol Ther 8(10):930-938.
Takai, et al., "Involvement of glypican-3 in the recruitment of M2-polarized tumor-associated macrophages in hepatocellular carcinoma." 2009, Cancer Biol Ther 8:2329-2338.
Tan et al., ""Superhumanized" antibodies: reduction of immunogenic potential by complementarity-determining region grafting with human germline sequences: application to an anti-CD28." 2002, J. Immunol., 169:1119-25.
Thapa, et al., "Childhood autoimmune hemolytic anemia following hepatitis E virus infection." 2009, J Paediatr Child Health 45:71-72.
Ui-Tei et al., "Sensitive assay of RNA interference in *Drosophila* and Chinese hamster cultured cells using firefly luciferase gene as target." 2000, FEBS Letters 479: 79-82.
Verbeeck, et al., "Evaluation of Versant hepatitis C virus genotype assay (LiPA) 2.0." 2008, J Clin Microbiol 46:1901-1906.
Verhoeyen et al., "Reshaping human antibodies: grafting an antilysozyme activity." 1988, Science, 239:1534-1536.
Vidali, et al., "Interplay between oxidative stress and hepatic steatosis in the progression of chronic hepatitis C." 2008, J Hepatol 48:399-406.
Ward et al., "Binding activities of a repertoire of single immunoglobulin variable domains secreted from *Escherichia coli*." 1989, Nature 331(6242):544-6.
Wu et al., "Humanization of a murine monoclonal antibody by simultaneous optimization of framework and CDR residues." 1999, J. Mol. Biol., 294:151-162.
Zhao, et al., "Rapid isolation of high-affinity human antibodies against the tumor vascular marker Endosialin/TEM1, using a paired yeast-display/secretory scFv library platform." 2011, J Immunol Methods 363:221-232.
Zhu et al., "Enhanced glypican-3 expression differentiates the majority of hepatocellular carcinomas from benign hepatic disorders." 2001, Gut 48(4):558-564.
Zittermann, et al., "Soluble glypican 3 inhibits the growth of hepatocellular carcinoma in vitro and in vivo." 2010, Int J Cancer 126:1291-1301.
Li et al., Supplement: The 62nd Annual Meeting of the American Association for the Study of Liver Diseases: The Liver Meeting 2011; abstracts first published online Sep. 30, 2011; Hepatology, vol. 54, Issue S1, pp. iiA-31A, 32A-1513A; Abstract 1951.

\* cited by examiner

US 9,790,267 B2

GLYPICAN-3-SPECIFIC ANTIBODY AND USES THEREOF

CROSS-REFERENCE TO RELATED APPLICATION

This is a continuation of PCT International Application No. PCT/US2012/062765, filed Oct. 31, 2012, which claims the benefit pursuant to 35 U.S.C. §119 (e) of U.S. Provisional Application No. 61/557,174, filed on Nov. 8, 2011, each of which are hereby incorporated by reference in their entirety herein.

STATEMENT REGARDING FEDERALLY SPONSORED RESEARCH OR DEVELOPMENT

This invention was made with government support under NIH NCI R21 CA149908 and NIH/NIDDKP30-DK050306 awarded by the National Institutes of Health (NIH). The government has certain rights in the invention.

BACKGROUND OF THE INVENTION

Hepatocellular carcinoma (HCC) is the fifth most common cancer and the third most common cause of cancer-related death worldwide (El-Serag, 2002, J Clin Gastroenterology 35:S72-78). During transformation from dysplastic regenerating hepatocytes to malignant hepatoma cells, several tumor-associated proteins are expressed that potentially could allow immune discrimination of malignant hepatocytes from surrounding non-tumor cells. Glypican-3 (GPC3), an oncofetal antigen re-expressed in a high frequency of neoplastic hepatocytes (Vidali, et al., 2008, J hepatol 48:399-406; Verbeeck, et al., 2008, J Clin Microbiol 46:1901-1906; Levrero, et al., 2009, J hepatol 51:581-592; Shaker, et al., 2009, Br J Dermatol 160:980-983) has emerged as a useful immunohistochemical diagnostic test (Anatelli, et al., 2008, Am J Clin Path 130:219-223; Baumhoer, et al., 2008, Am J Clin Path 129:899-906; Coston, et al., 2008, Am J Surg Pathol 32:433-444) and potential biomarker (Aburatani, 2005, J Gastroenterol 40, S16:1-6; Capurro, et al., 2005, Cancer Res 65:372; Capurro, et al., 2003, Gastroenterology 125:89-97; Hippo, et al., 2004, Cancer Res 64:2418-2423) for hepatocellular carcinoma. Glypican-3 appears critical for the association of growth factors such as IGF-2, BMP-7 and FGF-2 with growth factor receptors (Thapa, et al., 2009, J Paediatr Child Health 45:71-72; Zittermann, et al., 2010, Int J Cancer 126:1291-1301) but also may play an immunomodulatory role (Takai, et al., 2009, Cancer Biol Ther 8:2329-2338). Inhibition of glypican-3 function via knockdown (Ruan, et al., 2011, Int J Mol Med 28:497-503; Sun, et al., 2011, Neoplasia 13:735-747) or competition (Zittermann, et al., 2010, Int J Cancer 126:1291-1301; Feng, et al., 2011, Int J Cancer 128:2246-2247) has a profound negative effect on HCC cell line proliferation. Unlike any other tumor antigen associated with hepatocellular carcinoma to date, GPC3 is a glycophosphatidylinositiol-linked membrane-associated protein with a large extracellular domain attractive for antibody-directed therapy. An anti-glypican-3 antibody that induces antibody-dependent cytotoxicity has been shown to have anti-tumor effect in a xenograft animal model of hepatocellular carcinoma (Takai, et al., 2009, Cancer Biol Ther 8: 2329-38); this antibody has subsequently been humanized (Nakano, et al., 2010, Anticancer Drugs 21:907-916) and is entering human clinical trials. Thus the relative specific expressions of GPC3 on cell surface of malignant HCC tissues make it an attractive target for HCC tumor immunotherapy. However, the GPC3-specific T bodies, particularly the GPC3-specific scFv as targeting moieties, remain under development. The present invention addresses this need.

SUMMARY OF THE INVENTION

The invention provides an isolated polynucleotide encoding a human anti-GPC3 antibody or a fragment thereof comprising a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21.

In one embodiment, the isolated polynucleotide encoding a human anti-GPC3 antibody or a fragment comprises nucleic acid sequences for a heavy chain and light chain, wherein the nucleic acid sequence of the heavy chain is selected from the group consisting of SEQ ID NOs: 52-56 and the nucleic acid sequence of the light chain is selected from the group consisting of SEQ ID NOs: 57-61.

The invention also provides an isolated polypeptide encoding a human anti-GPC3 antibody or fragment thereof comprising a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21.

In one embodiment, the antibody fragment comprises a fragment selected from the group consisting of an Fab fragment, an F(ab')$_2$ fragment, an Fv fragment, and a single chain Fv (scFv).

The invention also provides a method for diagnosing a condition associated with the expression of GPC3 in a cell, the method comprising a) contacting the cell with a human anti-GPC3 antibody fragment comprising a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21; and b) detecting the presence of GPC3 wherein the presence of GPC3 diagnoses for a condition associated with the expression of GPC3.

The invention also provides a method of diagnosing, prognosing, or determining risk of liver cancer in a mammal, the method comprising detecting the expression of GPC3 in a sample derived from the mammal, the method comprising: a) contacting the sample with a human anti-GPC3 antibody fragment comprising a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21; and b) detecting the presence of GPC3 wherein the presence of GPC3 diagnoses for cancer in the mammal.

The invention also includes a method of inhibiting growth of a GPC3-expressing tumor cell, the method comprising contacting the tumor cell with a human anti-GPC3 antibody or a fragment thereof comprising a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21.

The invention also provides an isolated nucleic acid sequence encoding a chimeric antigen receptor (CAR), wherein the isolated nucleic acid sequence comprises the sequence of a human GPC3 binding domain and the sequence of a CD3 zeta signaling domain.

In one embodiment, the isolated nucleic acid sequence encoding a CAR comprises the sequence of a co-stimulatory signaling domain.

In one embodiment, the co-stimulatory signaling domain is selected from the group consisting of the CD28 signaling domain, the 4-1BB signaling domain, and any combination thereof.

In one embodiment, the human GPC3 binding domain is a human antibody or a fragment thereof selected from the group consisting of an Fab fragment, an F(ab')$_2$ fragment, an Fv fragment, and a single chain Fv (scFv).

In one embodiment, the antibody or a fragment thereof comprises a heavy chain and light chain, wherein the amino acid sequence of the heavy chain is selected from the group consisting of SEQ ID NOs: 12-16 and the amino acid sequence of the light chain is selected from the group consisting of SEQ ID NOs: 17-21.

In one embodiment, the antibody or a fragment thereof comprises nucleic acid sequences for a heavy chain and light chain, wherein the nucleic acid sequence of the heavy chain is selected from the group consisting of SEQ ID NOs: 52-56 and the nucleic acid sequence of the light chain is selected from the group consisting of SEQ ID NOs: 57-61.

The invention provides an isolated chimeric antigen receptor (CAR) comprising a human GPC3 binding domain and a CD3 zeta signaling domain.

In one embodiment, the CAR further comprises the sequence of a co-stimulatory signaling domain.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1C, is a series of images demonstrating target antigens applied to screen yeast display library. FIG. 1A is a schematic diagram of the primary structure of two antigen approaches selected from hGPC3 protein. The 29mer hGPC3$_{530-558}$ peptide and truncated hGPC3 fused with GST are represented by gray regions. Two glycosaminoglycan binding site (Gag) and putative glycosylphosphatidyl-inositol (GPI) anchor regions within the C-terminal hydrophobic region of hGPC3 are shown. FIG. 1B depicts an image of SDS-PAGE gel stained with Coomassie brilliant blue showing the expressed GST-fusion protein. BL21 bacteria transformed with the plasmid pGEX-4T/GPC3, encoding a GST-human/mouse GPC3 fusion protein, were induced to express the recombinant protein in presence of IPTG. Recombinant proteins were purified by glutathione agarose beads. The purified proteins (10 ul/each) were electrophoresed on a 10% SDS-PAGE gel for analysis. FIG. 1C is an image confirming of the purified recombinant protein by western blot. The purified recombinant protein were subjected to 10% SDS-PAGE and transferred to a nitrocellulose filter. The filter was probed with a commercial monoclonal anti-human GPC3 antibody (clone 1G12). Note the cross-reactivity of murine GPC3 with 1G12 control antibody.

FIG. 2A and FIG. 2B, is a series of images demonstrating enrichment of hGPC3-reactive scFvs.

FIG. 2A depicts surface co-localization of hGPC3-reactive yeast cells after two rounds of MACS-sorting. Yeast display library were incubated with target antigens and MACS sorting were performed. hGPC3-reactive yeast are double-labeled with mouse anti-c-myc detected with anti-mouse ALEXAFLUOR® 488, fluorescent dye secondary and biotinylated hGPC3-GST detected by streptavidin-phycoerythrin. FIG. 2B is an image demonstrating successful enrichment of hGPC3-reactive yeast cells by three rounds of FACS sorting. Representative FACS sorting using 29mer peptide hGPC3$_{530-558}$ antigen was shown. Gradually decreasing concentration of antigen was utilized in each round. Yeast cells without antigen incubation were used as control. In third FACS sorting, the PE-conjugated neutravidin was used in order to minimize enrichment of streptavidin-specific scFv also present in the library.

FIG. 3A through FIG. 3C, is a series of images demonstrating validation of scFv specificity by ELISA. FIG. 3A depicts preparation of soluble scFvs. scFv cDNA amplified from the enriched yeast population was co-transformed into YVH10 yeast using p416-BCCR vector. Yeast was induced to secrete scFvs with 2% galactose. Culture supernatant (5 µl) was loaded into SDS-PAGE gel for detection by anti-V5 mAb in Western Blot. Approximately 80% of yeast transformants produced soluble scFv. FIG. 3B depicts the results of ELISA screening of 576 scFv for binding to hGPC3-GST. Maxsorb plates were coated with hGPC3-GST and GST protein. scFvs were incubated in plates then washed extensively. HRP-conjugated anti-V5 mAb was used for quantification of binding. Each scFv was tested in parallel for binding to hGPC3-GST and GST. FIG. 3C depicts that scFvs with highest hGPC3-GST/GST binding ratio were screened for binding to full length hGPC3 protein expressed by mammalian cells.

FIG. 4A through FIG. 4C, is a series of images demonstrating affinity assessment of scFvs. FIG. 4A depicts the results of immunoblot analysis of binding of scFv to rhGPC3. The antigens including rhGPC3 and GST protein were spotted onto cellulose membrane (10 ng/each). After the blocking step the membrane were incubated with the scFvs antibody in room temperature for 1 h. The binding of scFv to antigen was detected by incubation with mouse anti-V5 mAb following by infrared dye IR680-labeled anti-mouse antibodies. PBS was used as negative control. FIG. 4B depicts results of direct ELISA for affinity determination of scFv 3E11. Two different concentrations of rhGPC3 protein (0.5 and 1.0 ug/ml) were coated and incubated with serial diluted scFv 3E11. For detection, mouse-sourced anti-V5 mAb following HRP-conjugated anti-mouse antibody and SureBlue substrate (measured at 450 nm) was used. FIG. 4C depicts EC50 values for 5 candidate scFvs determined by direct ELISA. Assays were performed twice separately for each scFv.

FIG. 5A through 5D, is a series of images demonstrating that scFvs specifically bind glypican-3-expressing cell lines. FIG. 5A is an image of a Western blot confirming the expression of glypican-3 in HepG2 and 293T.GPC3, knockdown in HepG2.sh57, and absence of expression in parental 293T and Hs578T. 1G12 antibody was used for detection. FIG. 5B is an image depicting the detection of hGPC3 expression on HepG2 and Hs578T cells by immunofluorescent microscopy using commercial 1G12 anti-GPC3 mAb followed by anti-mouse ALEXAFLUOR® 488, fluorescent dye. FIG. 5C is an image depicting binding of scFvs to HepG2 and Hs578T cells by flow cytometry using indicated scFv or 1G12 mAb followed by either APC-conjugated anti-V5 mAb or anti-mouse IR680 (for 1G12 only). Cells incubated with isotype antibody were used as negative control (grey area). FIG. 5D is an image of immunofluorescence of scFvs (detected with anti-V5 ALEXAFLUOR® 488, fluorescent dye) detected on HepG2.tdTomato.

FIG. 6A through FIG. 6E, is a series of images demonstrating scFv validation by HepG2 and HepG2-shRNA cell lines.

FIG. 6A depicts screening results of shRNAs for hGPC3 silencing. HEK 293 cells were transfected with shRNA-harboring pSIREN-ZsGreen vector and hGPC3$_{368-551}$-expressing plasmid. Expression of myc-tagged hGPC3$_{368-551}$ was assessed by Western blot using anti-myc antibody. GAPDH was used as control. FIG. 6B and FIG. 6C depict lower expression of hGPC3 in HepG2-sh57 expressing cells. Stable sh57 expression was established in HepG2 cell line via retroviral transduction. hGPC3 expression in these cells was detected by FACS using anti-GPC3 antibody (1G12) followed by anti-mouse APC. Unstained HepG2 cells (grey area), mouse isotype control-stained HepG2 (black line), HepG2 cells, and HepG2-sh57 are shown. The mean fluorescent intensity of 3E11 scFv binding in HepG2 and HepG2-sh57 cells were calculated in FIG. 6C. FIG. 6D depicts scFv binding to surface of HepG2 (black line) and HepG2-sh57 (grey area) cells demonstrated by FACS. Cells were incubated with the indicated scFvs and detected by APC-conjugated anti-V5 mAb. FIG. 6E, is a series of images of differential confocal immunoflurorescence staining of scFv with HepG2 (GFP-negative) and HepG2.sh57 (GFP-positive) cells. The cellular mixture of HepG2 and HepG2.sh57 (1:1) was cultured in slice chamber. Cells were stained with the indicated scFv and detected by anti-V5 mAb followed by anti-mouse ALEXAFLUOR® 546, fluorescent dye secondary antibody.

FIGS. 7A and 7B, is a series of images demonstrating the lack of impact that scFvs have on the proliferation of HepG2 cells. FIG. 7A is an image demonstrating validation of an MTT assay as a measurement of growth of HepG2. HepG2 and HepG2.sh57 cell lines that were grown for 4 days in culture. Manual counting with hematocytometer of trypsinized cells correlated strongly with MTT OD450 ($R^2$=0.99). FIG. 7B is an image demonstrating the effect of scFv on cell line proliferation. MTT OD450 for HepG2 cultured for 2 or 4 days in the presence or absence of 2E10, 3E11, 3D8, 4G5, and 2G9 at 1 µg/ml showed no evidence of growth inhibition.

FIG. 8A through 8D, is a series of images demonstrating generation of anti-hGPC3 chimeric antigen receptor engineered T cells. FIG. 8A is a diagram of lentiviral vectors encoding hGPC3-specific scFv-based CAR constructs. CARs with hGPC3-specific scFv fused with CD3t in combination with CD137 and/or CD28 costimulatory module or truncated CD3 (negative control) were constructed. FIG. 8B depicts western blotting of CAR CD3t expression in plasmid-transformed 293T cells. Lane 1: non-transduced cells as negative control; Lane 2: 3E11-dZ; Lane 3: 3E11-BBZ; Lane 4: 3E11-28BBZ. FIG. 8C depicts transduction efficiency of lentiviral particles in peripheral blood-isolated T cells. Lentivirus encoding GFP, prepared with the same conditions as the other lentivirus, were transduced into peripheral blood-isolated T cells from healthy donor. GFP expression in T cells was analyzed after two and ten days infection. FIG. 8D depicts flag expression on the surface of transduced T cells. One protein tag FLAG was inserted at the N-terminal of the lentiviral plasmid 3E11-28BBZ, and its expression on the 3E11-28BBZ len-tivirus-transduced T cells were detected by FACS using anti-Flag mAb following Alex-546-labelled secondary antibody.

FIGS. 10A and 10B, is a series of images depicting surface expression of GPC3 expression and antigen-specific lysis of GPC3-positive tumor cells. FIG. 10A depicts surface GPC3 expression as shown by solid black line in several human cancer cell lines by flow cytometry; isotype antibody as shown by grey area was used as negative control. FIG. 10B depicts antigen-specific lysis of GPC3-positive tumor cells by human T lymphocytes transduced with 3E11-CARs in Cr51-release assay at the indicated E/T ratio. 3E11-dZ transduced or GFP-transduced human T lymphocytes served as controls.

FIGS. 11A through 11C, is a series of images depicting schematics of a working model. FIG. 11A depicts that region against which scFvs for glypican-3 were developed and validated. FIG. 11B depicts structure of chimeric antigen receptor (CAR) and signaling domains. FIG. 11C depicts overall schema of redirecting T-cells based on CAR recognition of surface antigen to activate T-cells independent of T-cell receptor: HLA interactions.

FIG. 12A through 12D, is a series of images demonstrating scFv candidates generated against recombinant GPC3-GST fusion protein bind specifically glypican-3-expressing human cell lines. FIG. 12A depicts binding of candidate scFV by FACS to HepG2 (GPC3+) and 293T (GPC3−) cell lines. Either no scFv and no anti-V5 APC (gray shaded unstained control), no scFv plus anti-V5 APC (fluorochrome control), or 20 ul scFv-containing yeast culture supernatant plus anti-V5 APC as shown by black line were incubated×30 min, washed, then acquired on BD FACSCanto. FIG. 12B depicts binding of scFv to HepG2.tdTomato (red) detected by anti-myc ALEX-AFLUOR® 488, fluorescent dye. 1G12 is commercial positive control antibody. FIG. 12C depicts knockdown of GPC3 expression (90% by sh57) and reduction of scFv binding in shRNA57-transduced HepG2 cells. shRNA57 was constructed in bicistronic retroviral vector encoding GFP (left and right). scFv binding to cell membrane (center and right) is significantly reduced in GFP+ knocked-down HepG2 cells. FIG. 12D depicts binding affinity curves determined by ELISA. rhGPC3 at 1 ug/ml was precoated in 96 well plates and scFv added at 0.5-1 log dilutions over possible binding affinity range. EC50 were determined using antigen-antibody reaction equation.

FIG. 13A through FIG. 13C, is a series of images demonstrating generation of anti-hGPC3 chimeric antigen receptor engineered T cells. FIG. 13A depicts $^{51}$Cr assay incubating GPC3 CAR with HepG2.GFP2ALuc hGPC3+ cells. Transduction efficiency was approximately 50% for all constructs. FIG. 13B depicts knockdown abrogates killing by CAR T-cells against HepG2.sh57. FIG. 13C depicts the result of $^{51}$Cr assays of CAR transduced T-cells against HCE4 (hGPC3+), Hepa1-6 which expresses murine GPC3 homologue for which no cross-reactivity seen, hs578t (GPC3−) and K562 (GPC3−).

DETAILED DESCRIPTION

Figure 1:
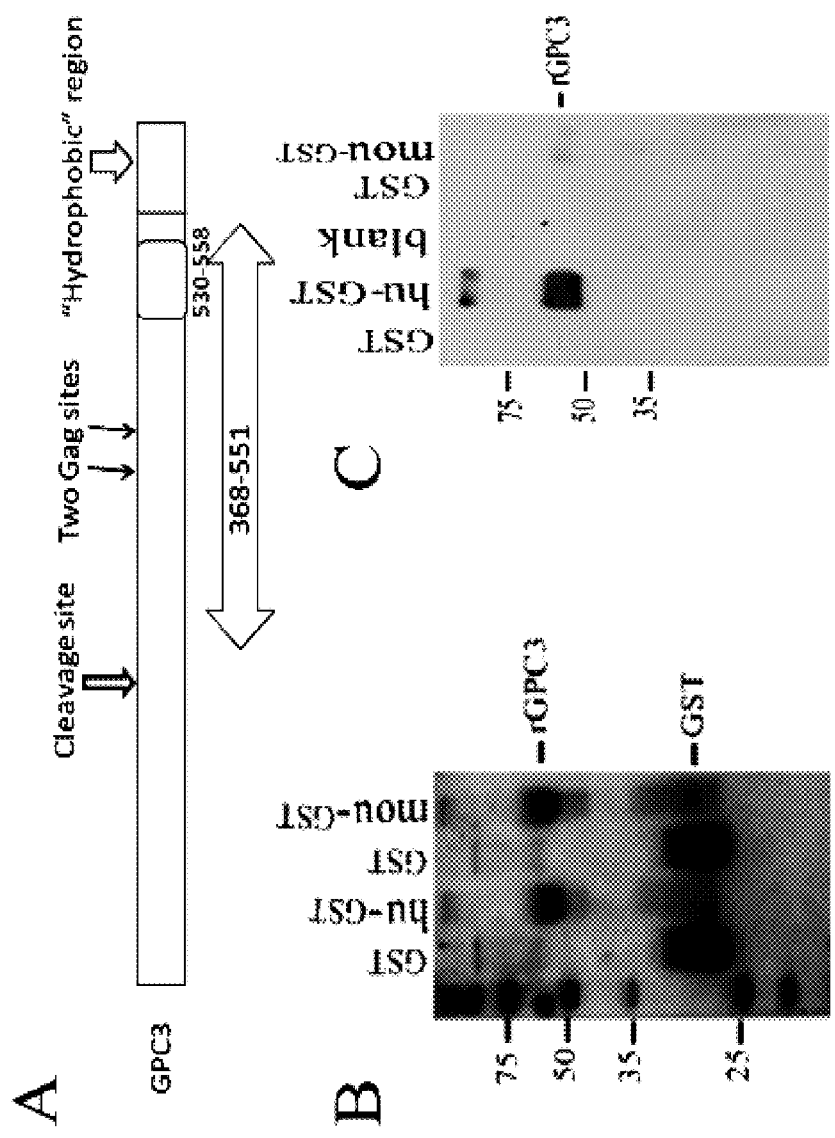
FIG. 1, comprising

The present invention is based partly on the identification of human-derived antibodies that specifically bind to glypican-3 (GPC3). The antibodies of the invention can be used for diagnostic and in vivo therapeutic applications. In embodiment, a peptide containing amino acids 530-558 or 368-548 of human GPC3 was used to screen a paired display/secretory yeast library to isolate human-derived scFv against GPC3.

In one embodiment, the scFv antibodies of the invention can be used for diagnosing the presence of GPC3 in a biological sample. In one embodiment, the scFv antibodies of the invention can be used for diagnosing the presence of GPC3 in a tumor cell.

In one embodiment, the scFv antibodies of the invention can be used for therapy against a disease, disorder or condition associated with dysregulation of GPC3 expression. In one embodiment, the scFv antibodies of the invention can be used for cancer therapy against cancers associated with dysregulated expression of GPC3.

The present invention relates generally to the treatment of a patient having a cancer associated with dysregulated expression of Glypican-3 (GPC3), or at risk of having a cancer associated with dysregulated expression of GPC3, using cellular infusion. In one embodiment, lymphocyte infusion, preferably autologous lymphocyte infusion is used in the treatment.

In one embodiment, PBMCs are collected from a patient in need of treatment and T cells therefrom are engineered and expanded using the methods described herein and then infused back into the patient. In another embodiment, autologous or heterologous NK cells or NK cell lines are engineered and expanded using the methods described herein and then infused back into the patient. The invention should not be limited to a particular cell or cell type. Rather, any cell or cell type can be engineered and expanded using the methods described herein and then infused back into the patient.

The present invention also relates generally to the use of T cells engineered to express a Chimeric Antigen Receptor (CAR). CARs combine an antigen recognition domain of a specific antibody with an intracellular signaling molecule. For example, the intracellular signaling molecule can include but is not limited to CD3-zeta chain, 4-1BB and CD28 signaling modules and combinations thereof. Preferably, the antigen recognition domain binds to GPC3. More preferably, the antigen recognition domain comprises a fully human anti-GPC3. Accordingly, the invention provides a fully human anti-GPC3-CAR engineered into a T cell and methods of their use for adoptive therapy.

In one embodiment, the invention includes autologous cells that are transfected with a vector comprising a fully-human anti-GPC3 CAR transgene. Preferably, the vector is a retroviral vector. More preferably, the vector is a self-inactivating lentiviral vector as described elsewhere herein.

In one embodiment, the anti-GPC3-CAR T cells of the invention can be generated by introducing a lentiviral vector comprising a GPC3 binding domain, CD8α hinge and transmembrane domain, and a CD3zeta signaling domain into the cells. In some instances, the vector further comprises the signaling domain of 4-1BB, CD28, or a combination of both. In one embodiment, the CAR-modified T cells of the invention are able to replicate in vivo resulting in long-term persistence that can lead to sustained tumor control.

In one embodiment, the scFv antibodies of the invention can be cloned into vectors that allow expression in cis with cellular cytotoxins. The combination of the scFv antibodies with cellular cytotoxins can be used for transarterial infusion into patients in need thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind glypican-3 using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of GPC3 refers to the level of expression or activity that is different from the expression level or activity of GPC3 in an otherwise identical healthy animal, organism, tissue, cell or component thereof. The term "dysregulated" also refers to the altered regulation of the level of expression and activity of GPC3 compared to the regulation in an otherwise identical healthy animal, organism, tissue, cell or component thereof "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, the terms "glypican-3," "glypican proteoglycan 3," "GPC3," are used interchangeably, and include variants, isoforms and species homologs of human Glypican-3. Accordingly, human antibodies of this disclosure may, in certain cases, cross-react with Glypican-3 from species other than human. In certain embodiments, the antibodies may be completely specific for one or more human Glypican-3 proteins and may not exhibit species or other types of non-human cross-reactivity. The complete amino acid sequence of an exemplary human Glypican-3 has Genbank/NCBI accession number NM004484.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GPC3.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides isolated antibodies, particularly human antibodies that bind specifically to GPC3. In certain embodiments, the antibodies of the invention comprise particular structural features such as CDR regions comprising particular amino acid sequences. The invention also provides methods of making such antibodies. The antibodies of the invention can be incorporated into an immunoconjugate, a chimeric antigen receptor (CAR), a pharmaceutical composition, and the like. In one embodiment, the immunoconjugates of the invention may be therapeutic agents, for example, cytotoxins or radioactive isotopes. Accordingly, the present invention provides compositions and methods for treating, among other diseases, cancer or any malignancy or autoimmune disease in which expression of GPC3 is dysregulated.

In one embodiment, the invention provides a cell (e.g., T cell) engineered to express a chimeric antigen receptor (CAR) wherein the CAR T cell exhibits an antitumor property. A preferred antigen is GPC3. In one embodiment, the antigen recognition domain of the CAR comprises a fully human anti-GPC3. Accordingly, the invention provides a fully human anti-GPC3-CAR engineered into a T cell and methods of their use for adoptive therapy.

In one embodiment, the anti-GPC3-CAR comprises one or more intracellular domain selected from the group of a CD137 (4-1BB) signaling domain, a CD28 signaling domain, a CD3zeta signal domain, and any combination thereof. This is because the present invention is partly based on the discovery that CAR-mediated T-cell responses can be further enhanced with the addition of costimulatory domains. For example, inclusion of the CD28 signaling domain significantly increased anti-tumor activity and in vivo persistence of CART cells compared to an otherwise identical CAR T cell not engineered to express CD28.

Anti-Glypican-3 (Anti-GPC3) Antibodies

The antibodies of the invention are characterized by particular functional features or properties of the antibodies. For example, the antibodies bind specifically to human Glypican-3. Preferably, the antibodies of the invention bind to Glypican-3 with high affinity, for example with an affinity EC50 ranging from about 5.0-110.9 nM. Preferably, the antibodies of the invention specifically recognize naturally expressed hGPC3 protein on a cell and do not cross-react to other surface proteoglycans.

In one embodiment, the antibodies of the invention are the human antibodies designated as 3E11, 2G9, 4G5, 3D8, and 2E10. The $V_H$ amino acid sequences of 3E11, 2G9, 4G5, 3D8, and 2E10 are shown in SEQ ID NOs: 12, 13, 14, 15, and 16, respectively (Table 2). The $V_L$ amino acid sequences of 3E11, 2G9, 4G5, 3D8, and 2E10 are shown in SEQ ID NOs: 17, 18, 19, 20, and 21, respectively (Table 2).

In one embodiment, the antibody contains heavy chain variable regions (Table 1) having CDRs 1, 2 and 3 consisting of the amino acid sequences set forth in SEQ ID NOs: in any of the following (a) to (e):
  (a) SEQ ID NOs: 22, 23, and 24 (3E11),
  (b) SEQ ID NOs: 25, 26, and 27 (2G9),
  (c) SEQ ID NOs: 28, 29, and 30 (4G5),
  (d) SEQ ID NOs: 31, 32, and 33 (3D8),
  (e) SEQ ID NOs: 34, 35, and 36 (2E10).

In one embodiment, the antibody contains light chain variable regions (Table 1) having CDRs 1, 2 and 3 consisting of the amino acid sequences set forth in SEQ ID NOs: in any of the following (f) to (j):

(f) SEQ ID NOs: 37, 38, and 39 (3E11),
(g) SEQ ID NOs: 40, 41, and 42 (2G9),
(h) SEQ ID NOs: 43, 44, and 45 (4G5),
(i) SEQ ID NOs: 46, 47, and 48 (3D8),
(j) SEQ ID NOs: 49, 50, and 51 (2E10).

Given that each of these antibodies can bind to Glypican-3, the $V_H$ and $V_L$ sequences can be "mixed and matched" to create other anti-Glypican-3 binding molecules of the invention. Glypican-3 binding of such "mixed and matched" antibodies can be tested using the binding assays described above and in the Examples (e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. It will be readily apparent to the ordinarily skilled artisan that novel VH and VL sequences can be created by substituting one or more VH and/or VL CDR region sequences with structurally similar sequences from the CDR sequences disclosed herein.

In one embodiment, the invention provides antibodies that comprise the heavy chain and light chain CDR1s, CDR2s and CDR3s of 3E11, 2G9, 4G5, 3D8, and 2E10, or combinations thereof.

In one embodiment, an antibody of the invention comprises heavy and light chain variable regions comprising amino acid sequences that are homologous to the amino acid sequences of the preferred antibodies described herein, and wherein the antibodies retain the desired functional properties of the anti-Glypican-3 antibodies of the invention.

For example, the invention provides an isolated antibody, or antigen binding portion thereof, comprising a heavy chain variable region and a light chain variable region, wherein: (a) the heavy chain variable region comprises an amino acid sequence that is at least 80% homologous to an amino acid sequence selected from the group consisting of SEQ ID NOs: 12, 13, 14, 15, and 16; (b) the light chain variable region comprises an amino acid sequence that is at least 80% homologous to an amino acid sequence selected from the group consisting of 17, 18, 19, 20, and 21. Preferably, the antibody binds to human Glypican-3 with an affinity of affinity EC50 ranging from 5.0-110.9 nM.

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 3E11, 2G9, 4G5, 3D8, and 2E10), or conservative modifications thereof, and wherein the antibodies retain the desired functional properties of the anti-Glypican-3 antibodies of the invention. Accordingly, the invention provides an isolated antibody (e.g., scFv), or antigen binding portion thereof, comprising a heavy chain variable region comprising CDR1, CDR2, and CDR3 sequences and a light chain variable region comprising CDR1, CDR2, and CDR3 sequences, wherein: (a) the heavy chain variable region CDR3 sequence comprises an amino acid sequence selected from the group consisting of amino acid sequences of SEQ ID NOs: 12, 13, 14, 15, and 16, and conservative modifications thereof; (b) the light chain variable region CDR3 sequence comprises an amino acid sequence selected from the group consisting of amino acid sequence of SEQ ID NOs: 17, 18, 19, 20, and 21, and conservative modifications thereof. Preferably, the antibody binds to human Glypican-3 with an affinity of affinity EC50 ranging from 5.0-110.9 nM.

In another embodiment, the invention provides antibodies that bind to the same epitope on human Glypican-3 as any of the Glypican-3 antibodies of the invention (i.e., antibodies that have the ability to cross-compete for binding to Glypican-3 with any of the antibodies of the invention). In preferred embodiments, the reference antibody for cross-competition studies can be one of the antibodies described herein (e.g., 3E11, 2G9, 4G5, 3D8, and 2E10). Such cross-competing antibodies can be identified based on their ability to cross-compete with 4A6, 11E7, or 16D10 in standard Glypican-3 binding assays. For example, Biacore analysis, ELISA assays or flow cytometry may be used to demonstrate cross-competition with the antibodies of the current invention. The ability of a test antibody to inhibit the binding of, for example, 3E11, 2G9, 4G5, 3D8, or 2E10, to human Glypican-3 demonstrates that the test antibody can compete with 3E11, 2G9, 4G5, 3D8, or 2E10 for binding to human Glypican-3 and thus binds to the same epitope on human Glypican-3 as 3E11, 2G9, 4G5, 3D8, or 2E10.

An antibody of the invention further can be prepared using an antibody having one or more of the VH and/or VL sequences disclosed herein can be used as starting material to engineer a modified antibody, which modified antibody may have altered properties as compared to the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

CAR Composition

The present invention encompasses a recombinant DNA construct comprising sequences of an antibody of the invention that binds specifically to human glypican-3, wherein the sequence of the antibody or a fragment thereof is operably linked to the nucleic acid sequence of an intracellular domain. The intracellular domain or otherwise the cytoplasmic domain comprises, a costimulatory signaling region and/or a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

The present invention encompasses a recombinant DNA construct comprising sequences of a fully human CAR, wherein the sequence comprises the nucleic acid sequence of a GPC3 binding domain operably linked to the nucleic acid sequence of an intracellular domain. An exemplary intracellular domain that can be used in the CAR includes but is not limited to the intracellular domain of CD3-zeta, CD28, 4-1BB, and the like. In some instances, the CAR can comprise any combination of CD3-zeta, CD28, 4-1BB, and the like.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR. In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like. Preferably, the cancer is hepatocellular carcinoma (HCC).

In one embodiment, the tumor antigen of the present invention comprises one or more antigenic cancer epitopes immunologically recognized by tumor infiltrating lymphocytes (TIL) derived from a cancer tumor of a mammal.

In a preferred embodiment, the antigen binding moiety portion of the CAR targets glypican-3, preferably human glypican-3.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-glypican-3 antibodies directed against the human glypican-3 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the present invention, the ability to bind human glypican-3. However, using certain methods of humanization, the affinity and/or specificity of binding of the antibody for human glypican-3 may be increased using methods of "directed evolution," as described by Wu et al., J. Mol. Biol., 294:151 (1999), the contents of which are incorporated herein by reference herein in their entirety.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, N Y 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 ($3^{rd}$ ed., Cold Spring Harbor Press, N Y 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as FICOLL® density separation media. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL® density gradient separation media or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated magnetic beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH® (an anti-CD52 antibody), anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH® (an anti-CD52 antibody). In another embodiment, the cells are isolated prior to and can be frozen for later use for treatment following B-cell ablative therapy such as agents that react with CD20, e.g., RITUXAN® (an anti-CD20 antibody).

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-VIVO 15®, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V® (serum free media), DMEM, MEM, α-MEM, F-12, X-VIVO 15™ (serum-free hematopoietic cell media), and X-VIVO 20™ (serum-free hematopoietic cell media), OPTMIZER™ (T-cell expansion media), with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a method of inhibiting growth of a GPC3-expressing tumor cell, comprising contacting the tumor cell with at least one antibody or a fragment thereof of the invention such that growth of the tumor cell is inhibited.

In one embodiment, the invention pertains to a method of inhibiting growth of a GPC3-expressing tumor cell, comprising contacting the tumor cell with an anti-GPC3 CAR T cell of the present invention such that growth of the tumor cell is inhibited.

In another aspect, the invention pertains to a method of treating cancer in a subject. The method comprises administering to the subject an antibody or a fragment of the invention or an anti-GPC3 CAR T cell of the present invention such that the cancer is treated in the subject. Particularly preferred cancers for treatment are hepatocellular carcinomas, pancreatic cancers, ovarian cancers, stomach cancers, lung cancers and endometrial cancers. In still other embodiments, the cancer to be treated is selected from the group consisting of hepatocellular carcinomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the fully-human CAR transduced T cells exhibit specific proinflammatory cytokine secretion and potent cytolytic activity in response to human cancer cells expressing the GPC3, resist soluble GPC3 inhibition, mediate bystander killing and mediate regression of an established human tumor. For example, antigen-less tumor cells within a heterogeneous field of GPC3-expressing tumor may be susceptible to indirect destruction by GPC3-redirected T cells that has previously reacted against adjacent antigen-positive cancer cells.

The fully-human CAR-modified T cells of the invention may be a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with dysregulated expression of GPC3. In certain embodiments, the cells of the invention are used in the treatment of patients at risk for developing diseases, disorders and conditions associated with dysregulated expression of GPC3. Thus, the present invention provides methods for the treatment or prevention of diseases, disorders and conditions associated with dysregulated expression of GPC3 comprising administering to a subject in need thereof, a therapeutically effective amount of the fully human CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH® (an anti-CD52 antibody). In another embodiment, the cell compositions of the present invention are administered following B-cell ablative therapy such as agents that react with CD20, e.g., RITUXAN® (an anti-CD20 antibody). For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH® (an anti-CD52 antibody), for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

Diagnostic Method

In another aspect, the present invention provides a method of diagnosing a disease such as cancer by detecting GPC3 protein in a test sample with the use of the antibody of the present invention.

The detection used herein includes quantitative detection and non-quantitative detection. The non-quantitative detection include, for example, determination of merely whether or not GPC3 protein is present, determination of whether or not a specific amount or more of GPC3 protein is present, determination for comparison of the amount of GPC3 protein with that of another sample (e.g., a control sample). The quantitative detection includes determination of the concentration of GPC3 protein, determination of the amount of GPC3 protein.

The test sample is not particularly limited as long as it is a sample that may contain GPC3 protein, however, preferred is a sample collected from the body of a living organism such as a mammal, and more preferred is a sample collected from human. Specific examples of the test sample may include, for example, blood, interstitial fluid, plasma, extravascular fluid, cerebral fluid, joint fluid, pleural fluid, serum, lymph fluid, saliva, preferably blood, serum and plasma. In addition, a sample obtained from the test sample such as culture solution of cells collected from the body of the living organism is also included in the test sample of the present invention.

The cancer to be diagnosed is not particularly limited, and specific examples may include liver cancer, pancreatic cancer, lung cancer, colon cancer, mammary cancer, prostate cancer, leukemia and lymphoma, preferably liver cancer. GPC3 to be detected is not particularly limited, and may be either full-length GPC3 or a fragment thereof. In the case where a fragment of GPC3 is detected, it may be either the N-terminal fragment or the C-terminal fragment.

The method of detecting GPC3 protein contained in a test sample is not particularly limited, however, detection is preferably performed by an immunological method with the use of an anti-GPC3 antibody. Examples of the immunological method include, for example, a radioimmunoassay, an enzyme immunoassay, a fluorescence immunoassay, a luminescence immunoassay, immunoprecipitation, a turbidimetric immunoassay. Preferred is an enzyme immunoassay, and particularly preferred is an enzyme-linked immunosorbent assay (ELISA) (e.g., a sandwich ELISA). The above-mentioned immunological method such as an ELISA can be carried out by a method known to those skilled in the art.

A general detection method with the use of an anti-GPC3 antibody comprises immobilizing an anti-GPC3 antibody on a support, adding a test sample thereto, incubating the support to allow the anti-GPC3 antibody and GPC3 protein to bind to each other, washing the support, and detecting the GPC3 protein binding to the support via the anti-GPC3 antibody to detect GPC3 protein in a test sample.

The binding between the anti-GPC3 antibody and the GPC3 protein is generally carried out in a buffer. Buffers used in the invention include, for example, a phosphate buffer, a Tris buffer. Incubation is carried out under the conditions generally employed, for example, at 4° C. to room temperature for 1 hour to 24 hours. The washing after incubation can be carried out by any method as long as it does not inhibit the binding between the GPC3 protein and the anti-GPC3 antibody, using for example a buffer containing a surfactant such as TWEEN 20®.

In the method of detecting GPC3 protein of the present invention, a control sample may be provided in addition to a test sample to be tested for GPC3 protein. The control samples include a negative control sample that does not contain GPC3 protein and a positive control sample that contains GPC3 protein. In this case, it is possible to detect GPC3 protein in the test sample by comparing the result obtained with the negative control sample that does not contain GPC3 protein with the result obtained with the positive control sample that contains GPC3 protein. It is also possible to quantitatively detect GPC3 protein contained in the test sample by obtaining the detection results of the control samples and the test sample as numerical values, and comparing these numerical values.

One preferred embodiment of detecting GPC3 protein binding to the support via an anti-GPC3 antibody is a method using an anti-GPC3 antibody labeled with a detectable label. For example, GPC3 protein may be detected by contacting the test sample with an anti-GPC3 antibody immobilized on the support, washing the support, and then detecting GPC3 with the use of the labeled antibody that specifically binds to GPC3 protein.

The labeling of an anti-GPC3 antibody can be carried out by a generally known method. Examples of the detectable label known to those skilled in the art include a fluorescent dye, an enzyme, a coenzyme, a chemiluminescent substance or a radioactive substance. Specific examples may include radioisotopes ($^{32}P$, $^{14}C$, $^{125}I$, $^{3}H$, $^{131}I$ and the like), fluorescein, rhodamine, dansyl chloride, umbelliferone, luciferase, peroxidase, alkaline phosphatase, beta-galactosidase, beta-glucosidase, horseradish peroxidase, glucoamylase, lysozyme, saccharide oxidase, microperoxidase, biotin and the like. In the case where biotin is used as a detectable label, it is preferred that a biotin-labeled antibody is added, and then avidin conjugated to an enzyme such as alkaline phosphatase is further added.

Specifically, a solution containing an anti-GPC3 antibody is added to a support such as a plate to allow the anti-GPC3 antibody to be immobilized. After washing, the plate is blocked with, for example, BSA in order to prevent the nonspecific binding of a protein. The plate is washed again, and then the test sample is added to the plate. After being incubated, the plate is washed, and then the labeled anti-GPC3 antibody is added. After being incubated appropriately, the plate is washed, and then the labeled anti-GPC3 antibody remaining on the plate is detected. The detection of the protein can be carried out by a method known to those skilled in the art. For example, in the case where the antibody is labeled with a radioactive substance, the protein may be detected by liquid scintillation or the RIA method. In the case where the antibody is labeled with an enzyme, the protein may be detected by adding a substrate and detecting an enzymatic change of the substrate such as color development with an absorbance reader. In the case where the antibody is labeled with a fluorescent substance, the protein may be detected with the use of a fluorometer.

A particularly preferred embodiment of the method of detecting GPC3 protein of the present invention is a method using an anti-GPC3 antibody labeled with biotin and avidin. Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein. The plate is washed again, and then the test sample is added to the plate. After being incubated, the plate is washed, and then the biotin-labeled anti-GPC3 antibody is added. After being incubated appropriately, the plate is washed, and then avidin conjugated to an enzyme such as alkaline phosphatase or peroxidase is added. After being incubated, the plate is washed, and then a substrate of the enzyme conjugated to avidin is added. Then, GPC3 protein is detected by means of the enzymatic change of the substrate as an indicator.

Another embodiment of the method of detecting GPC3 protein of the present invention is a method using a primary antibody that specifically binds to GPC3 protein and a secondary antibody that specifically binds to the primary antibody. For example, the test sample is brought into contact with an anti-GPC3 antibody immobilized on the support, the support is incubated and washed, and the bound GPC3 protein after washing is detected with a primary anti-GPC3 antibody and a secondary antibody that specifically binds to the primary antibody. In this case, the secondary antibody is preferably labeled with a detectable label.

Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein. The plate is washed again, and then the test sample is added to the plate. After being incubated, the plate is washed, and then a primary anti-GPC3 antibody is added. After being incubated appropriately, the plate is washed, and then a secondary antibody that specifically binds to the primary antibody is added. After being incubated appropriately, the plate is washed, and then the secondary antibody remaining on the plate is detected. The detection of the secondary antibody can be carried out by the above-mentioned method.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Glypican-3-Specific scFv Isolation and Validation for Use in Hepatocellular Carcinoma The following experiments were designed to develop and validate GPC3-specific T bodies. The high throughput methodology used in these experiments identified human-derived scFvs with $EC_{50}$ ranging from 5.0-110.9 nM that bound specifically to glypican-3-expressing cell lines and whose binding was significantly reduced by shRNA knockdown of glypican-3. These scFvs are optimal for development for diagnostic and in vivo therapeutic applications.

Briefly, two different biotinylated antigen targets, a synthesized 29mer fragment $GPC3_{550-558}$ and a truncated $GPC3_{368-548}$ fused with GST, was used to screen a yeast display library which was enriched to greater than 30% target-specific yeast with both positive selection and depletion of streptavidin- and GST-specific clones. After cloning identified scFv cDNA from the enriched sublibrary, scFv specificity was validated by ELISA for binding to recombinant protein from prokaryotic and eukaryotic sources and ultimately naturally-presented human protein on the cell membrane of human hepatocellular cell lines. Specificity was confirmed using non-expressing cell lines and shRNA knockdown. Ultimately, five unique scFv with affinity $EC_{50}$ ranging from 5.0-110.9 nM were identified. These results demonstrate characterization of five novel and unique scFvs for potential humoral or chimeric therapeutic development in human hepatocellular carcinoma.

The materials and methods employed in these experiments are now described.

Materials and Methods

Cell Lines and Media

Cell lines of 293T (ATCC, Manassas Va.), HepG2 (ATCC), Hep3B (obtained from the Penn Center for Molecular Studies in Digestive and Liver Disease) and GP2-293 cells (Clontech, Mountain View, Calif.) were maintained in Dulbecco's modified essential medium DMEM (Invitrogen, Carlsbad, Calif.) with 10% fetal bovine serum (FBS, Sigma, St. Louis Mo.). HepG2.tdTomato were generated via stable transfection of parental HepG2 with lentivirus-harboring tdTomato Red and purified by flow cytometry. 293T.GPC3 were generated by cloning full-length human GPC3 cDNA (NM_004484) into pDisplay (Invitrogen) XmaI and SacII sites using the following forward (5' CCCGGGGCCACCTGTCACCAAGTCCG 3' SEQ ID NO: 62) and reverse primer (5' CCGCGGGTG-CACCAGGAAGAAGAAGCAC 3' SEQ ID NO: 63).

Inducible Expression and Purification of Truncated hGPC3 Protein

The full-length cDNA of human glypican-3 (NM_004484) was amplified from a human cDNA library using the following forward primers (5' ATGGCCGGGAC CGTGCGCACC 3') (SEQ ID NO: 1) and reverse primer (5' TCAGTGCACCAGGAA GAAGAAGCA 3') (SEQ ID NO: 2). A 594 bp DNA fragment corresponding to the region of nt1277-1871, which translates a truncated fragment of hGPC3 (aa 368-548) between the CRD cleavage site and putative transmembrane domain, was cloned into the prokaryotic expression vector pGEX-4T using SalI and EcoRI restriction sites (forward primer: 5'CCG GAA TTC GAC AAG AAA GTA TTA AAA GTT GCT CA 3'(SEQ ID NO: 3) and reverse primer: 5' ACG CGT CGA CGG TGC TTA TCT CGT TGT CCT TC-3') (SEQ ID NO: 4) to generate a plasmid encoding a truncated hGPC3-GST recombinant fusion protein under the control of an IPTG-inducible tac promoter. The plasmid was transformed into E. coli BL21-CODONPLUS® (DE3)-RIPL (Stratagene, Santa Clara Calif.), grown in fresh 2YT medium, and induced by 1 mM IPTG at 25° C. for 6 hours. Bacterial cells were collected by centrifugation and lysed by sonication in presence of 1% sarkosyl and 2% TRITON™ X-100 (a surfactant). The lysate was incubated with Glutathione SEPHAROSE® 4B beads (a gel filtration matrix) (GE healthcare, Piscataway N.J.) at 4° C. for 4 hours, washed, and then eluted 50 mM Tris-HCl buffer (pH 7.4) containing 20 mM reduced glutathione. The recovery of the GST and GPC3-GST fusion protein was monitored by Coomassie Blue staining. The trhGPC3-GST, GST, and a commercially custom synthesized 29mer GPC3 peptide (aa 530-558, Proimmune Oxford UK) were biotinylated using NHS Biotinylation kit (Pierce, Rockford Ill.).

Selection of hGPC3-Reactive scFvs by Screening Paired Yeast-Display/Secretory scFv Library The paired yeast-display/secretory scFv library has previously been described (Zhao, et al., 2011, J Immunol Methods 363:221-232; Scholler, et al., 2006, J Immunol Methods 317, 132-143), and was screened using existing methodology with minor modifications. Briefly the yeast display library was grown in SD-CAA (2% raffinose, 0.67% yeast nitrogen base, and 0.5% casamino acids) at 30° C. to an Å600 of ~5. Surface scFv expression was induced by re-inoculating yeast at an Å600 of 0.5 in SGRD-CAA (SD-CAA+2% galactose) and grown at 20° C. for 16-36 h. scFv expression by yeast was confirmed by flow cytometry using anti-c-myc mouse mAb (9E10, Santa Cruz biotechnology) and goat anti-mouse Fab ALEXAFLUOR 488®, fluorescent dye (AF488, Invitrogen, Carlsbad Calif.). Two rounds of magnetic bead-based selection were performed as follows: $1 \times 10^9$ induced yeast cells in 500 ul PBE buffer (PBS+0.5% EDTA) were incubated with biotinylated 29mer GPC3 peptide (100 nM) or biotinylated rhGPC3-GST (100 ng/ml) at 25° C. for 30 min then on ice for 10 min. The rhGPC3-reactive scFv were enriched by magnetically sorting over an LS column (Miltenyi Biotec, Auburn, Calif.). When screening with rhGPC3-GST protein, GST-reactive yeast were depleted over an LS column after incubation of induced yeast with biotinylated GST and streptavidin microbeads. Three rounds of flow cytometry-based sorting were performed with gradually decreasing concentration of target antigen as follows: yeast cells were stained with mouse anti-c-myc mAb (1:200), anti-mouse IgG1 AF488, biotinylated antigen (rhGPC3 protein at 40 ng/ml in $1^{st}$ round, 20 ng/ml in $2^{nd}$ round, and 10 ng/ml in $3^{rd}$ round), and either streptavidin-PE ($1^{st}$ and $2^{nd}$ round, Invitrogen) or NEUTRA-VIDIN®-PE ($3^{rd}$ round, Invitrogen). AF488+ and PE+ double positive yeast were selected and recovered in 96 well plates containing SD-CAA.

High Throughput Purification of Secreted scFvs scFv cDNA were extracted from the enriched yeast population after the $3^{rd}$ round of flow sorting, amplified by PCR (forward primer: 5'-GGTTCTGGTGGTGGAG GTTCTG-GTGGTGGTGGATCTG-3(SEQ ID NO: 5); reverse 5'-GA-GACCGAGGAGAGGGTTAGGGATAGGCTTACCGT CGACCAAGTCTTCTTCAGAATAAGCTT-3'(SEQ ID NO: 6)), purified using MiniElute kit (Qiagen, Valencia Calif.), and then cotransformed with 100 ng of linearized p416-BCCR vector into YVH10 cells. Transformed yeast were plated on Trp+SD-CAA dishes, from which approximately six hundred colonies were transferred to growth medium in deep 96-well plates (Fisher Scientific) and induced by 2% galactose to secrete scFv for up to 72 h. For high throughput purification of scFv, yeast culture supernatant (720 ul) with 80 ul 10× equilibration buffer (0.05M sodium phosphate and 0.3M sodium chloride, pH 8.0) was transferred into a new clean deep 96-well plate and incubated with HIS-Select-Nickle Affinity Gel (10 ul) for 1 h at 4° C. All supernatant were then transferred to pre-wet Multi-screen-HV filter plates (Millipore, Billerica Mass.) and drained with a vacuum manifold. After washing, scFv were eluted using 50 mM sodium phosphate pH 8.0, 0.3M sodium chlorate and 250 mM imidazole and vacuum transferred into polypropylene 96 well plates.

ELISA and Measurement scFv Affinity by ELISA

For measurement of scFv affinity, Nunc Maxisorb plates were pre-coated with hGPC3-GST protein at the indicated concentration in carbonate-bicarbonate buffer overnight at 4° C. After three washing steps with PBS/0.1% TWEEN-20® (PBST) (a surfactant), 300 ul per well of blocking solution (2% milk in PBS pH 7) was added for 2 h at room temperature then washed three times with PBST. Candidate scFv starting at 100 ug/ml were added with serial dilutions, incubated for 1 h at room temperature followed by three washing steps with PBST. scFv binding was detected by adding anti-V5 HRP (Invitrogen), washing×4 with PBST, washing×1 with PBS, then adding 50 ul/well of TMB peroxidase substrate (KPL, Gaithersburg Md.) plus peroxidase substrate solution B at 1:1 ratio, then the reaction was stopped using 50 ul of 0.5M $H_2SO_4$. OD450 was measured using a BioRad 680 microplate reader. For determination of functional affinity, half maximal binding concentration (EC50) was calculated with non-linear regression curve fit algorithm using the software program PRISM (GraphPad Software, San Diego, Calif.). rhGPC3 expressed in a murine myeloma cell line which was commercially obtained from R&D Systems (Minneapolis Minn.).

Flow Cytometry

Detection of scFv binding to cell lines was detected with anti-V5 mAb (AbD Serotec, Raleigh, N.C.). Anti-hGPC3 mAb (1G12, Biomosaics Inc., Burlington, Vt.) was used as a positive control. scFvs were premixed with anti-V5 APC mAb (AbD Serotec) at a molar ratio of 1:1 for 30 min at RT. scFv-anti-V5 complexes were then incubated with target cell lines for 30 min at 37° C. Cells were then acquired on a FACSCanto (Becton Dickinson, San Jose Calif.) and analyzed using FlowJo (Treestar, Ashland, Oreg.).

Confocal Immunofluorescence

Target cell lines cultured on 0.2 µm coverslips (Nunc, Rochester, N.Y.) were fixed and stained with the indicated scFv-V5 APC complex. Image acquisition was performed on a Fluoview 10 confocal laser microscope (Olympus).

Western and Dot Blot

Cell lysates were separated by SDS-PAGE gel and transferred to polyvinylidene difluoride membranes (PVDF). In a dot blot procedure, purified protein (10 ng) was spotted on PVDF membrane. Membranes were blotted with primary Abs followed by incubation with infrared dye IR680-labeled secondary antibodies and quantified using LI-COR Odyssey software.

Glypican-3 Knockdown hGPC3-specific short hairpin RNAs (shRNAs) were prepared in the pSIREN-retroQ-zsGreen retroviral vector using BD knockout RNAi systems according to the manufacturer's instruction (Clontech). Three pairs of 21 nt oligonucleotides, named sh56, sh57, and sh58 as well as a LacZ (negative control), were predicted according to Ambion SILENCER® Select software, annealed and subcloned into pSIREN-retroQ-zsGreen at the BamHI and EcoRI sites. The RNA targeting sequence of these three shRNAs are (sh56: 5'-GCCAAATTATTCTCC TATGTT-3'(SEQ ID NO: 7); sh57: 5'-GCCAATATAGA TCTGCTTATT-3'(SEQ ID NO: 8); sh58: 5'-GCTCAAGAA AGATGGAAGAAA-3' (SEQ ID NO: 9)). For testing hairpin silencing, myc-tagged hGPC3$_{(AA\ 368-551)}$ was cloned into the Display plasmid. Plasmids expressing shRNA and hGPC3.myc plasmids were co-transfected into HEK 293 cells (3:1 ratio, hairpin to target), and cells were lysed after 48 h. hGPC3.myc levels were quantified by Western blot using anti-c-myc mAb. Pseudotyped retrovirus encoding shRNA were then produced. Briefly, GP2-293 cells were seeded in 10 cm cell culture dishes 12 h prior to transfection. At 50% density, cells were transfected with bug pSIREN-shRNA plasmid and 5 ug pVSV-G (Clontech) for pseudotyping using the calcium phosphate transfection method. On day 2 and day 3 after transfection, media containing retroviral particles were collected. Particles were concentrated 100-fold by ultracentrifugation. To infect cells, 10 ul of concentrated virus stock were added into 1×10⁶HepG2 cells in presence of polybrene (4 ug/ml). Transduced cells were isolated by FACS sorting of eGFP+ cells and maintained as stable cell lines.

MTT
(4,5-dimethylthiazol-2-yl)-2,5-diphenyltetrazolium Bromide) Assay

A standard MTT assay using the CELLTITER 96® Non-Radioactive Cell Proliferation Assay (Promega Corporation, Madison Wis.) according to manufacturer's instructions was performed. HepG2 and HepG2.sh57 cells were plated at a density of 5×10³ cells/well in triplicate in a 96-well plate and incubated for 2-4 days as indicated. Optical density was measured at 570 nm. Trypisinized cells were manually counted by hematocytometer in validation experiments.

The results of the experiments are now described.
Preparation of Target Antigen for Screening of hGPC3-Specific scFv Two target antigens were developed for scFv isolation. First, a 29mer peptide hGPC3$_{530-558}$ was chosen and commercially synthesized in biotinylated and non-biotinylated formats to develop scFvs specific for the region between two C-terminal GAG modification sites and the hydrophobic putative GPI-linkage domain predicted by an online algorithm as depicted in FIG. 1. Second, a truncated hGPC3$_{368-548}$-GST fusion protein spanning a larger region of the C-terminus of the protein was expressed and purified as depicted in FIG. 1. Purity of the expressed fusion protein was further confirmed by Western blot with the 1G12 mAb as depicted in FIG. 1C. Both the 29mer hGPC3$_{530-558}$ and hGPC3$_{368-548}$-GST were biotinylated for yeast library screening.

Isolation of hGPC3-Reactive scFV-Displaying Yeast

Figure 2:
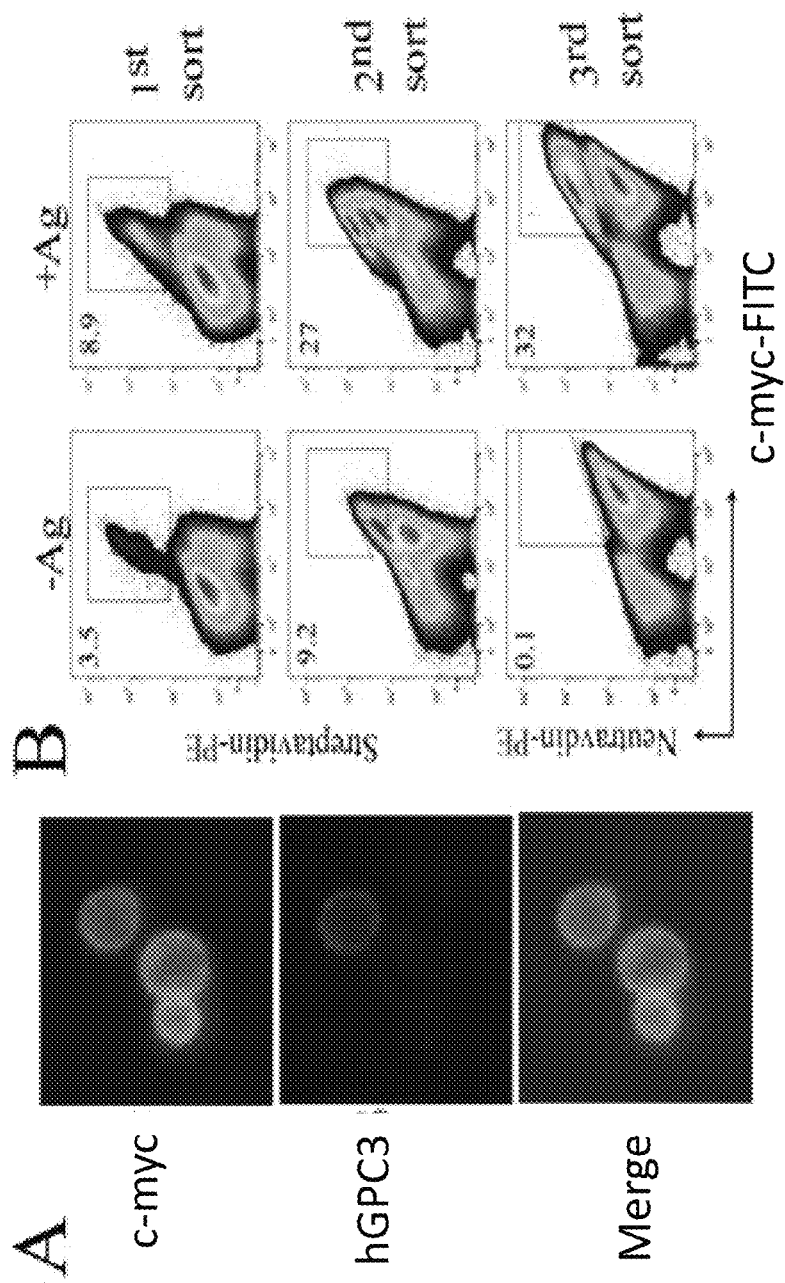
FIG. 2, comprising

The yeast library was subjected to two rounds of magnetic-sorting using biotinylated hGPC3$_{530-558}$ or three rounds of magnetic-sorting using biotinylated hGPC3$_{368-548}$-GST to enrich hGPC3-specific scFv-expressing yeast. The third magnetic sort of hGPC3$_{368-548}$-GST was a depletion sort to eliminate GST-specific scFv-expressing yeast using biotinylated GST. The enriched sub-library was then further enriched for hGPC3-specific scFv-expressing yeast with three rounds of flow sorting selecting for yeast expressing scFv-c-myc and biotinylated antigen at progressively decreasing concentration as depicted in FIG. 2A. Streptavidin-PE was used to identify scFv specific for biotinylated target in the first two rounds. NEUTRAVIDIN®-PE was utilized in the third round to eliminate selection of streptavidin-specific scFv-expressing yeast (~9% of yeast after MACS and two rounds of FACS sorting). This strategy yielded a marked enrichment of hGPC3-reactive yeast to approximately 30% of the population as depicted in FIG. 2B.

Selection of hGPC3-Specific scFv by ELISA

Figure 3:
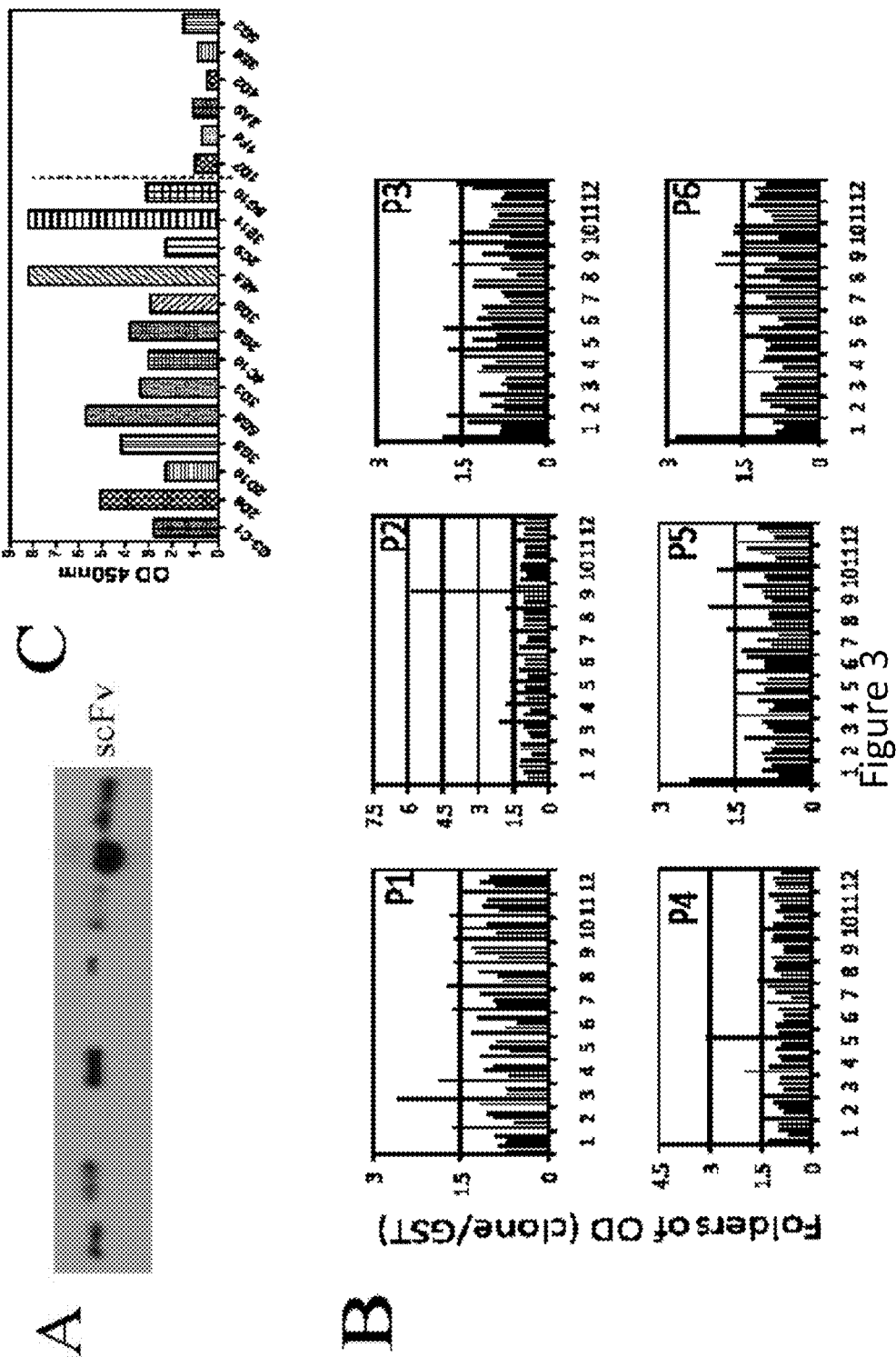
FIG. 3, comprising

The majority of yeast clones obtained after transduction of scFv cDNA cloned into a secretory plasmid produced scFv at detectable quantities in supernatant (FIG. 3A).

Approximately 300 transformed yeast colonies were subcultured for high-throughput Ni-purification of supernatant. The 300 scFv candidates were then assessed for binding to rhGPC3 by ELISA as depicted in FIG. 3B. In order to eliminate GST-reactive scFv, each scFv candidate was tested in parallel for binding to both GST and rhGPC3-GST. Thirty-six scFv candidates with ODhGPC3-GST/ODGST ratios greater than 1.5 were selected for further screening as depicted in FIG. 3B. Binding to full-length glycosylated recombinant hGPC3 protein expressed in a murine myeloma cell line was assessed by ELISA as depicted in FIG. 3C. Thirteen candidates with $OD_{GPC3}/OD_{media}$ ratio greater than 2 were identified.

Biological Characterization of the scFv Candidates

Figure 4:
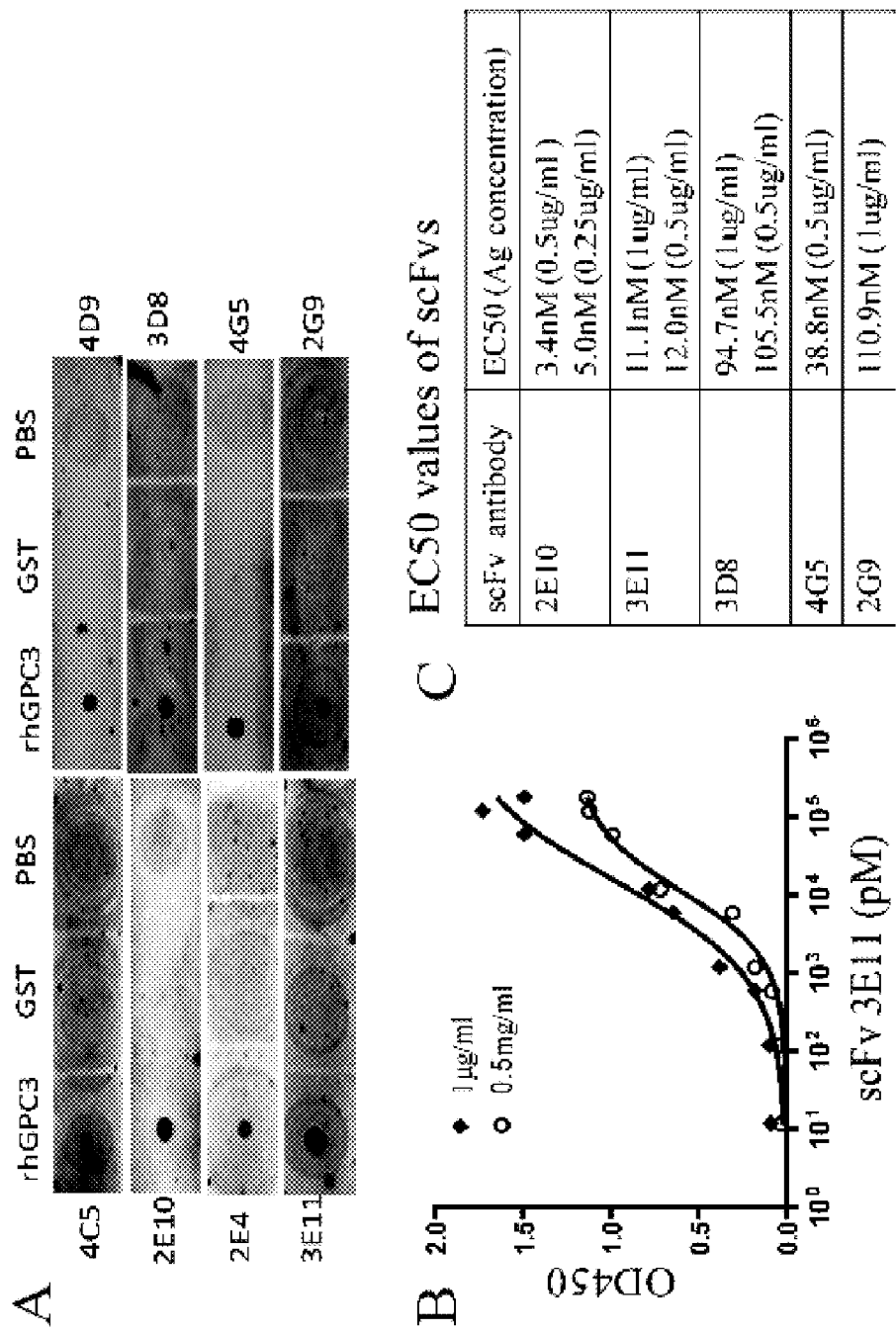
FIG. 4, comprising

Among these thirteen scFv candidates, eight yeast colonies with varying ELISA affinity were chosen for further validation. Soluble scFv were purified from the supernatant by anti-HIS chromatography resulting in 0.1-0.5 mg soluble antibody/liter culture. Using a dot blot analysis, all scFv recognized rhGPC3 protein with no cross-reactivity with GST protein as depicted in FIG. 4A, confirming ELISA findings. Nucleotide sequencing of these thirteen scFv yeast colonies revealed five unique sequences, for which 2E10, 3E11, 3D8, 4G5, and 2G9 represented one of each clone (Table 2). The analysis of the predicted amino acid sequence by alignment of scFv heavy and light chain variable region sequence to a database of human immunoglobulin germline sequences (V base directory of human V gene sequences) using IgBLAST®, sequence search tool, was applied to establish VH and VL gene utilization and heavy-chain CDR composition of the scFv antibodies as shown in Table 1. The VH domains in scFv 2G9, 4G5 and 2E10 are VH IV, while 3E11 and 3D8 are VHIII. For VL domain, 3E11 is LV1kvII, 4G5 is KV3; and the remaining are KV2. The binding affinity for rhGPC3 was established by ELISA at two concentrations of rhGPC3 protein and repeated, with affinity determined by calculation of half maximal binding concentration (EC50) using a non-linear regression curve-fit algorithm. The EC50 value of scFv ranged from 3 nM to 105 nM. For scFv 3E11, the comparable affinities were measured to be 14 nM at the concentration of 1 ug/ml and 11 nM at the concentration of 0.5 ug/ml rhGPC3 protein as shown in FIGS. 4B and 4C.

TABLE 1

Sequence analysis of anti-GPC3 scFv

| scFvs clone | Subtype heavy chain | CDR1 (SEQ ID NO:) | CDR2 (SEQ ID NO:) | CDR3 (SEQ ID NO:) | Numbers of nucleotide difference |
|---|---|---|---|---|---|
| VH: | | | | | |
| 3E11 | HV3 | SYGLH (22) | AISYDGSKKYYADSVKG (23) | GWFVEPLS (24) | 13 |
| 2G9 | HV4 | SSSYYWA (25) | NIYYSGSTYYNPSLKS (26) | FPLIRGYRYRYDEY (27) | 6 |
| 4G5 | HV4 | SGYYWG (28) | RIYYGGSTHYNPSLQS (29) | DRNYQSLSGYCLDY (30) | 16 |
| 3D8 | HV3 | SYAMS (31) | AISGSGTSTYYADSVKG (32) | HKSFGVQWL (33) | 26 |
| 2E10 | HV4 | SSSYYWG (34) | SIYYSGSTYYNPSLKS (35) | HDGHRYGTYYGLDV (36) | 15 |
| VL: | | | | | |
| 3E11 | LV1 | SGSSSNIGSNTVN (37) | SNNQRPS (38) | GWFVEPLS (39) | 4 |
| 2G9 | KV2 | RSSQSLLHRDGYHYLN (40) | LGSNRAS (41) | MQAPQTPRT (42) | 9 |
| 4G5 | KV3 | RASQSVSSHIA (43) | GASTRAT (44) | QQYNKWPP (45) | 11 |
| 3D8 | KV2 | WSSQSLVYGDGNTYLN (46) | KVSNRDS (47) | MQGTHWPPG (48) | 4 |
| 2E10 | KV2 | SSQSLVYSDGNTYLN (49) | KVSNRDS (50) | MQGTHWPP (51) | 10 |

Amino acid sequences of the VH and VL antigen binding regions of the scFv were analyzed by alignment of a database of immunoglobulin germline sequence.
The complementary determining regions (CDRs) are provided.
The number of nucleotide differences from germline database is also tabulated.

TABLE 2

Sequence identifiers for anti-GPC3 scFV

| SEQ ID NO: # | IDENTITY |
|---|---|
| SEQ ID NO: 12 | 3E11; heavy chain (amino acid) |
| SEQ ID NO: 13 | 2G9; heavy chain (amino acid) |
| SEQ ID NO: 14 | 4G5; heavy chain (amino acid) |
| SEQ ID NO: 15 | 3D8; heavy chain (amino acid) |

TABLE 2-continued

Sequence identifiers for anti-GPC3 scFV

Figure 5:
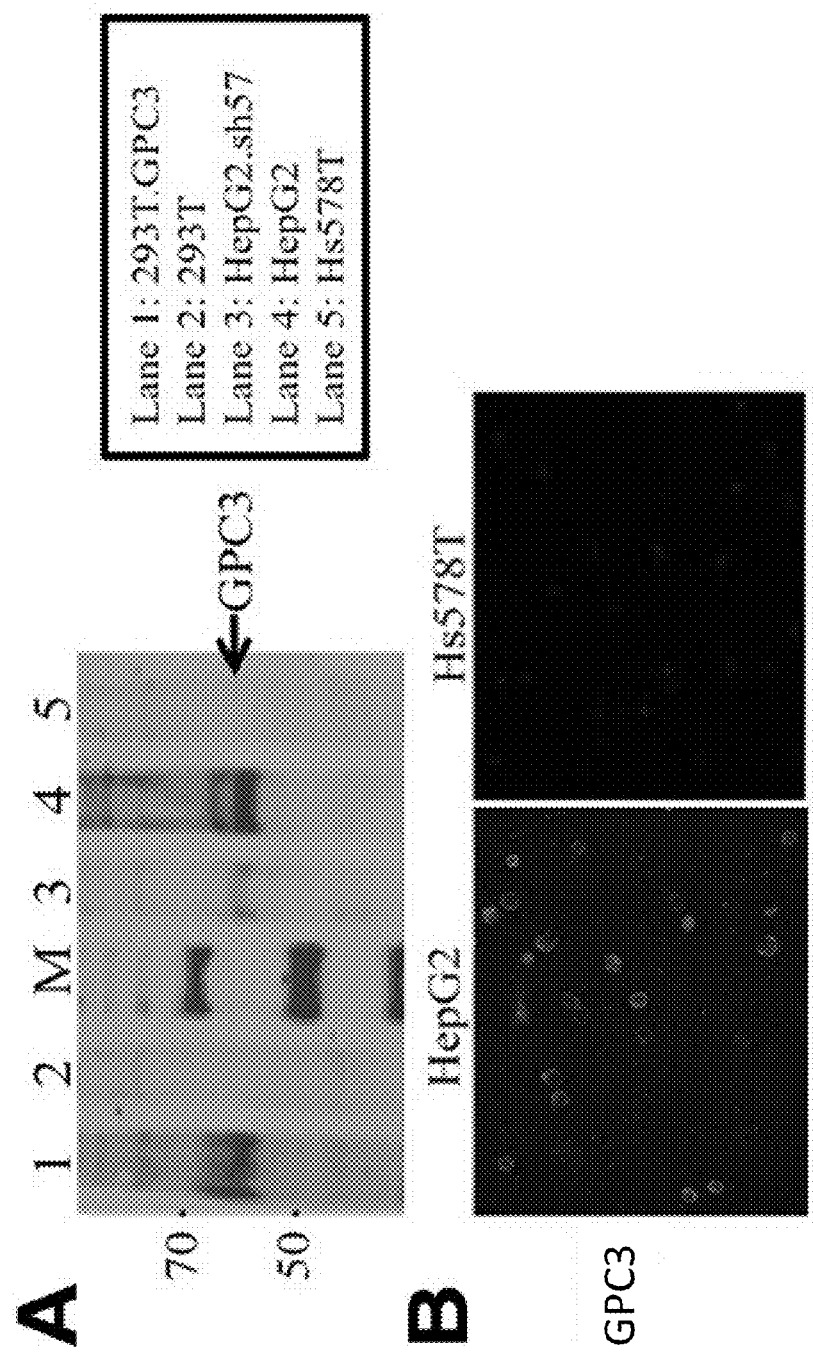
FIG. 5, comprising
Figure 5:
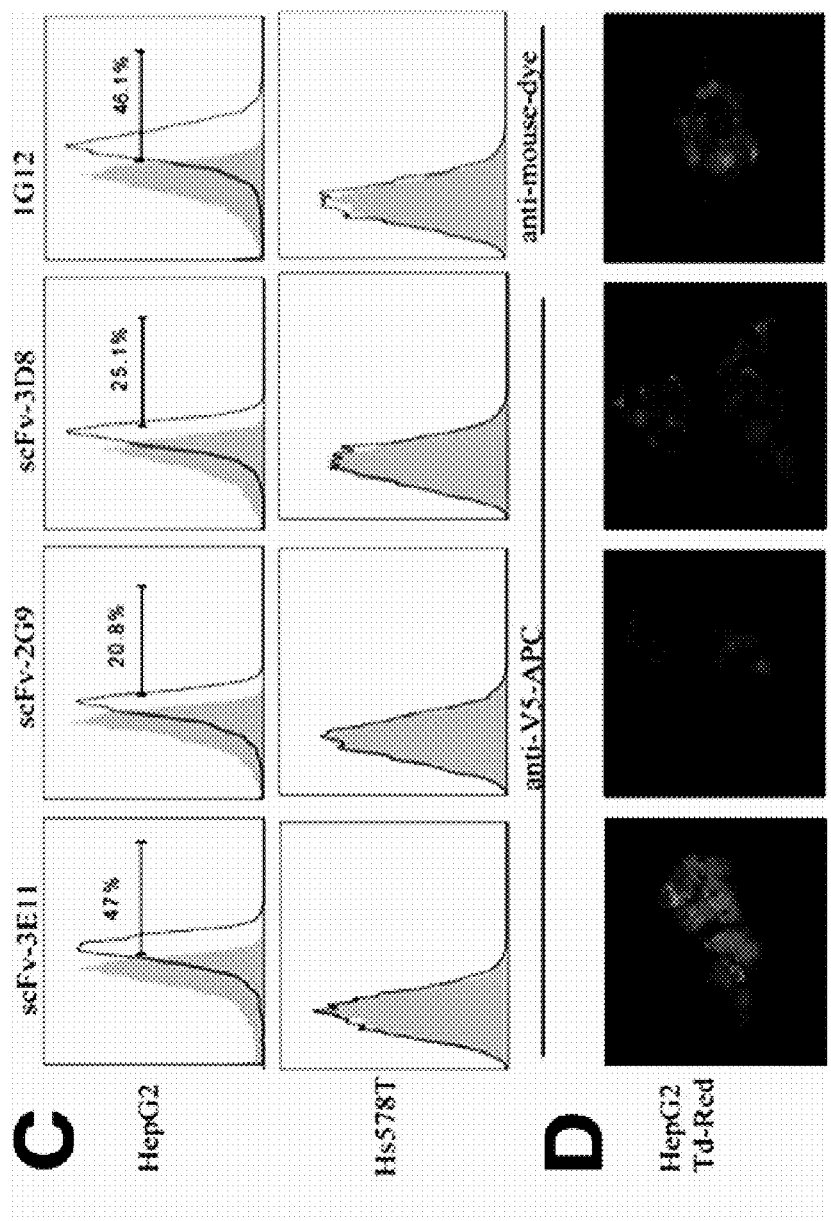

| SEQ ID NO: # | IDENTITY |
| --- | --- |
| SEQ ID NO: 16 | 2E10; heavy chain (amino acid) |
| SEQ ID NO: 17 | 3E11; light chain (amino acid) |
| SEQ ID NO: 18 | 2G9; light chain (amino acid) |
| SEQ ID NO: 19 | 4G5; light chain (amino acid) |
| SEQ ID NO: 20 | 3D8; light chain (amino acid) |
| SEQ ID NO: 21 | 2E10; light chain (amino acid) |
| SEQ ID NO: 22-51 | CDR1, CDR2, CDR3 of anti-GPC3 scFv |
| SEQ ID NO: 52 | 3E11; heavy chain (nucleotide) |
| SEQ ID NO: 53 | 2G9; heavy chain (nucleotide) |
| SEQ ID NO: 54 | 4G5; heavy chain (nucleotide) |
| SEQ ID NO: 55 | 3D8; heavy chain (nucleotide) |
| SEQ ID NO: 56 | 2E10; heavy chain (nucleotide) |
| SEQ ID NO: 57 | 3E11; light chain (nucleotide) |
| SEQ ID NO: 58 | 2G9; light chain (nucleotide) |
| SEQ ID NO: 59 | 4G5; light chain (nucleotide) |
| SEQ ID NO: 60 | 3D8; light chain (nucleotide) |
| SEQ ID NO: 61 | 2E10; light chain (nucleotide) | scFv Binding to Native hGPC3 Protein Specifically on Human Cell Surface on Glypican-3-Expressing Cell Lines The next experiments were performed to test scFv binding to naturally-expressed surface hGPC3. scFvs including 3E11, 2G9 and 3D8 were complexed with anti-V5 APC and incubated with HepG2 (glypican-3+), 293T (glypican-3-negative) or Hs578T (glypican-3-negative) cell lines, which were then washed and assessed by flow cytometry. As shown in FIG. 5B, all three scFvs exhibited a range of binding affinity to endogenous surface-expressed hGPC3 on HepG2, while no binding was found on 293T or Hs578T cells. Binding was also confirmed by immunofluorescence microscopy as depicted in FIG. 5C using HepG2.tdTomato and Hs578t.tdTomato cells. The transduction of tdTomato protein did not alter GPC3 expression in HepG2 cells. scFv-3E11, 2G9 and 3D8 showed intense membrane immunofluorescence staining with a significant fraction of viable HepG2.tdTomato cells. All these data suggests that these three scFvs can specifically recognize naturally expressed hGPC3 protein and absence of cross-reactivity to other surface proteoglycans.

Validation of scFvs' Specificities in RNAi-Based Cell Binding

Figure 6:
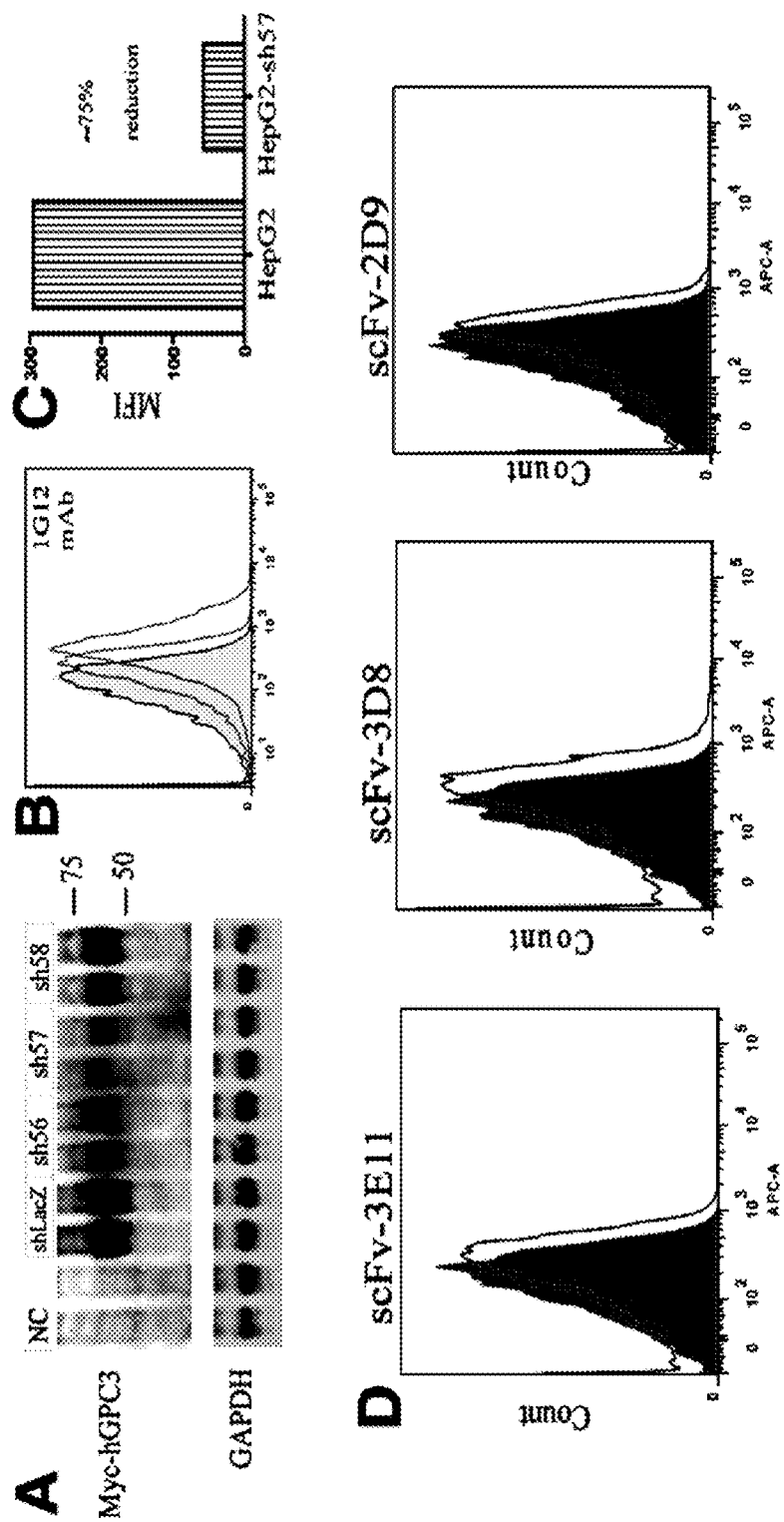
FIG. 6, comprising
Figure 6:
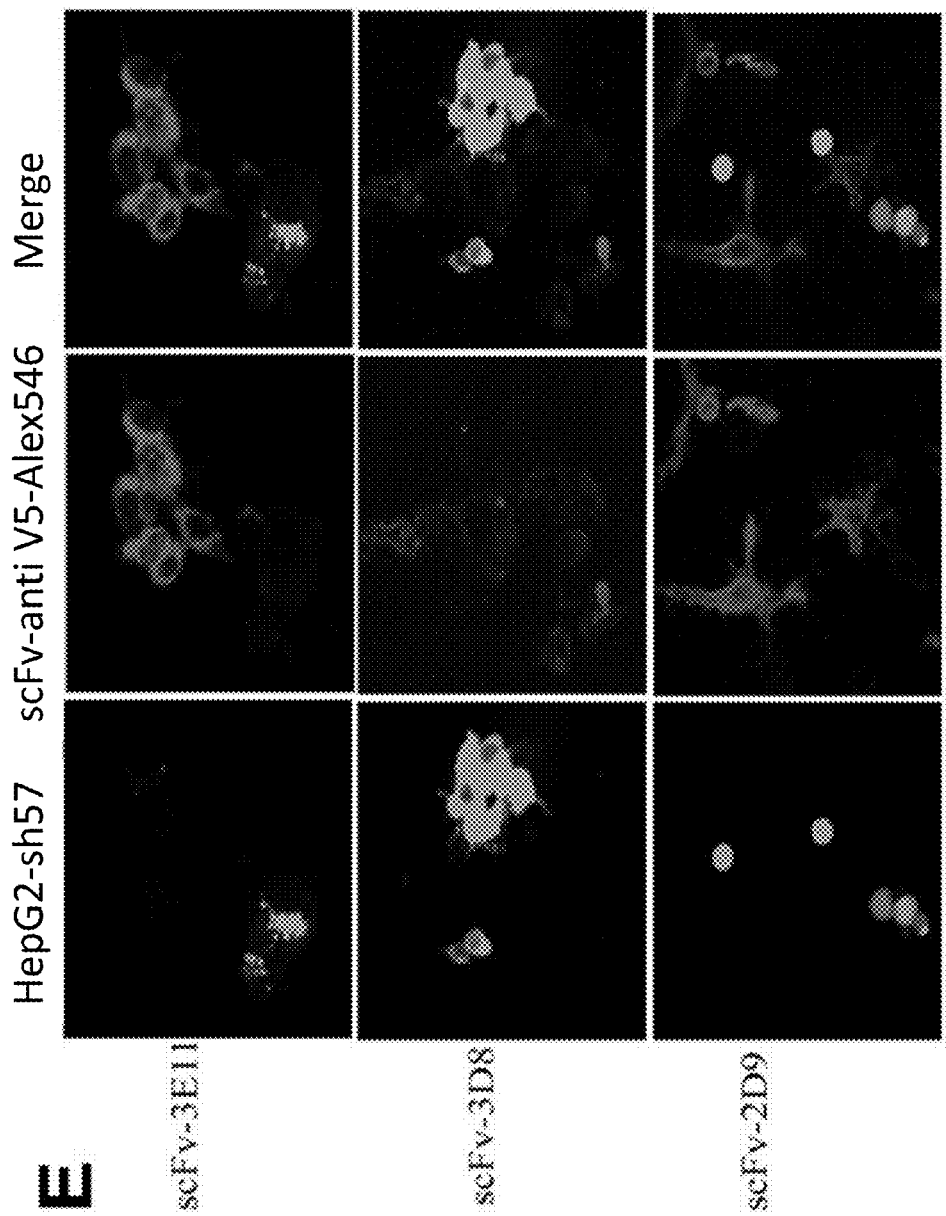

To further confirm the specificity for scFv binding to hGPC3, GPC3-shRNA transduced HepG2 cells were used. Silencing was confirmed by co-expressing a plasmid encoding myc-tagged hGPC3(AA 368-551) with three shRNA candidate vectors in 293T cells. sh57 showed the best silencing efficiency, reducing hGPC3 protein levels up to 80% compared to the scrambled control as depicted in FIG. 6A. sh57 was then retrovirally transduced into HepG2 cells in a GFP-expressing vector to generate HepG2.sh57 stable cell line. HepG2.sh57 markedly reduced surface glypican-3 expression by approximately 75% reduction of MFI when detected with 1G12 as depicted in FIG. 6B and FIG. 6C. scFvs including 3E11, 2G9, 3D8, 2E10 and 4G5 were incubated with HepG2 and HepG2.sh57 cells, respectively, and detected by APC-labeled anti-V5 mAb. As shown in FIG. 6D, significant reduction of binding between HepG2 and HepG2.sh57 cells was observed with scFv-3E11, 2G9 and 3D8, while the staining with scFv-2E10 and 4G5 had no detectable differences. These findings were confirmed by immunoflurorescence staining in which a 1:1 mixture of HepG2 and HepG2.sh57 cells were stained with scFv as depicted in FIG. 6E. Cell membrane staining by scFvs was profoundly reduced in HepG2.sh57 relative to wild-type HepG2 cells.

Glypican-3-Specific scFv are not Cytostatic

Figure 7:
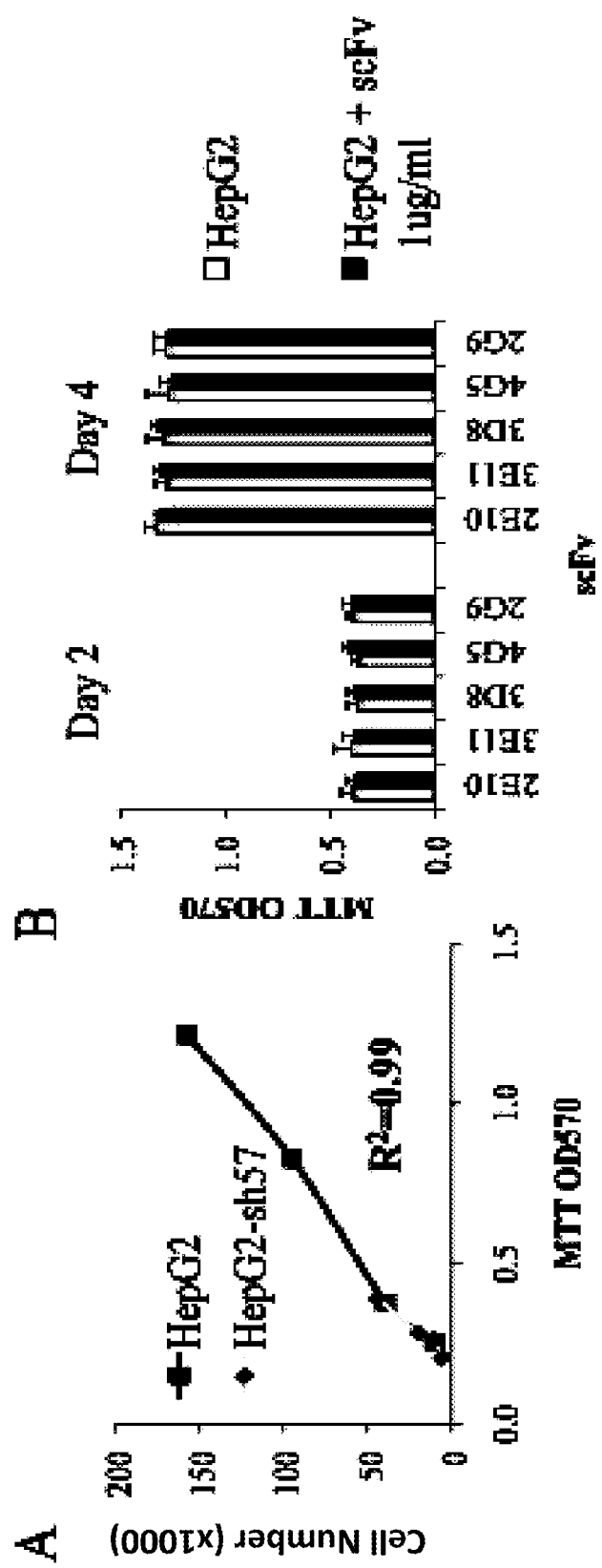
FIG. 7, comprising

To determine if scFv binding to membrane-associated glypican-3 alters cellular proliferation, a standard MTT assay was performed after validation of the accuracy of MTT to measure proliferation of HepG2 cells. It was observed that no positive or negative impact on proliferation of the glypican-3-expressing HepG2 cell line was detected with any scFv at high concentration (1 ug/ml) (FIG. 7).

Validation of Glypican-3-Specific scFv Isolated from Paired Display/Secretory Yeast Display Library Therapeutic options for hepatocellular carcinoma (HCC) remain limited particularly in advanced stages. Immunotherapy with NK- or T-cell augmenting therapies to date has yielded some early promising results (Korangy et al., 2010 Expert Rev Gastroenterol Hepatol 4(3): 345-353; Greten et al. 2010 BMC Cancer 10: 209; Palmer et al., 2009 Hepatology 49(1): 124-132; Barkholt et al., 2009 Immunotherapy 1(5): 753-764) but the low affinity of endogenous tumor-specific T-cell receptors and the immunosuppressive milieu of the tumor microenvironment represent barriers to effectively harnessing the power of the endogenous immune system to control cancer. Yeast-derived scFv offer many advantageous properties for the development of anti-tumor biologics. scFv are inexpensive to produce, easily modifiable e.g. biotinylation (Scholler et al., 2006 J Immunol Methods 317(1-2):132-143), and facile for subsequent cloning in cis with diagnostic or effector domains.

Identification of an appropriate tumor-associated antigen is an obviously essential requirement for scFv development. Glypican-3 (GPC3), a heparan-sulfate proteoglycan, has recently been identified as a highly specific, membrane-associated tumor antigen found in 49-100% of HCC (Zhu et al., 2001 Gut 48(4): 558-564; Capurro et al., 2003 Gastroenterology 125(1): 89-97; Sung et al., 2003 Cancer Sci 94(3): 259-262; Nakatsura et al., 2003 Biochem Biophys Res Commun 306(1): 16-25). GPC3 is not expressed (or is expressed very focally (Abdul-Al et al., 2008 Hum Pathol 39(2): 209-212)) in nontumorous cirrhotic liver tissue (Baumhoer et al., 2008 Am J Clin Pathol 129(6): 899-906; Filmus et al., 2004 Mol Diagn 8(4): 207-212) and expression of GPC3 in other normal tissues appears limited (Baumhoer et al., 2008 Am J Clin Pathol 129(6): 899-906). GPC3 modulates the effect of growth factors such as IGF-2, BMP-7 and FGF-2 on hepatoma cells (Midorikawa et al., 2003 Int J Cancer 103(4): 455-465; Zittermann et al., 2010 Int J cancer J int du cancer 126(6): 1291-1301) and may recruit M2 tumor-promoting macrophages to the HCC microenvironment (Takai et al., 2009 Cancer Biol Ther 8(24): 2329-2338). Emerging evidence also suggests that inhibition of glypican-3 function via knockdown (Roan et al., 2011 Int J Mol Med 28(4): 497-503; Sun et al., 2011 Neoplasia 13(8): 735-747) or competition (Zittermann et al., 2010 Int J cancer J int du cancer 126(6): 1291-1301; Feng et al., 2011 Int J cancer J Int du cancer 128(9): 2246-2247) has a profound negative effect on HCC proliferation. Expression on the cell surface makes GPC3 an attractive target for antibody-directed therapy. Another group has shown that a murine anti-hGPC3 antibody induces antibody-dependent cytotoxicity that manifests an anti-tumor effect in a xenograft animal model of hepatocellular carcinoma (Takai et al., 2009 Cancer Biol Ther 8(10): 930-938); this antibody has subsequently been humanized (Nakano et al., 2010 Anti-cancer drugs 21(10): 907-916) and is entering human clinical trials. Thus, available evidence suggests that glypican-3 is a rational target for humoral and potentially chimeric immunotherapy for HCC.

In this study, the paired display/secretion yeast system was used to isolate five candidate scFv with affinity in the range from 5.0-110.9 nM that each demonstrates specificity for binding the surface of glypican-3-expressing cell lines. scFv binding was significantly reduced after specific knockdown of glypican-3. The paired yeast display/secretion system minimizes post-translational and conformational changes in the conversion from displayed to soluble scFvs, a property that allows for consistency during the high throughput screening and validation process (Zhao et al., 2011 J Immunol Methods 363(2): 221-232). scFv specificity to the naturally processed glypican-3 protein at physiological conditions was critical given complex post-translational modifications of glypican-3. Experiments were performed to utilized increasingly physiological screening criteria to select scFv candidates for further evaluation. Dramatic differences of scFv binding between wild-type and glypican-3-knockdown HepG2 in cell culture conditions confirmed not only the specificity of scFv binding but also the capacity to bind to naturally-processed cell surface glypican-3 in situ. Without wishing to be bound by any particular theory, experiments can be performed to validate a chimeric antigen receptor to redirect T-cells against glypican-3-expressing targets using the 3E11 scFv.

Not surprisingly, scFv had no direct positive or negative impact on cellular proliferation unlike that demonstrated by soluble glypican-3 (Zittermann et al., 2010 Int J cancer 126(6): 1291-1301). The relatively small size of scFv (27 Id)) makes competitive inhibition of growth factor binding unlikely.

Glypican-3 is a rational target in hepatocellular carcinoma for antibody-based therapy. The results presented herein demonstrate that five unique scFv with affinity ranging from 5.0-110.9 nM were identified. Each scFv demonstrated strong surface binding to glypican-3-expressing cell lines that was attenuated by shRNA knockdown, and did not bind glypican-3-nonexpressing cell lines.

Example 2: GPC3-Specific CAR Generation and Lentivirally-Transduced Human T Lymphocytes The following experiments were performed to validate a chimeric antigen receptor to redirect T-cells against glypican-3-expressing targets using the 3E11 scFv.

The materials and methods employed in these experiments are now described.
Materials and Methods
GPC3-Specific CAR Generation and Lentivirally-Transduced Human T Lymphocytes The cDNA of 3E11 scFv was amplified from yeast colonies using the primers (forward primer: 5' ggatccGTCCAGTCTGTGTTGACG CAGC 3' (SEQ ID NO: 10) and reverse primer: 5' gctagcTGAGGAGACGGTGACCAG TGTTC 3' (SEQ ID NO: 11)), and was inserted into the lentiviral vector pELNs/CARs by BamHI and NheI to generate lentiviral vector pELNs/3E11-CARs. See FIG. 8.
Lentiviral Vectors 293T cells ($5 \times 10^6$) were plated on 10-cm dish pre-coated with 0.002% poly-L-lysine (Sigma, St. Louis Mo.). The lentiviral vector pELNS/3E11-CARs were co-transfected with the plasmid pMD.G, pMDLg/pRRE, and pRSV-Rev. After 12 h, the medium was changed. After a further 24 h, virus-containing supernatant was collected and passed through a 0.45 μm filter. Then, supernatant was concentrated by ultracentrifugation at 25,000 rpm, tittered and stored at −80 C until use.

Lentiviral Transduction of Human T Lymphocytes

Primary human T lymphocytes isolated from healthy donors were acquired from the Human Immunology Core at University of Pennsylvania. T cells were cultured in complete medium (RPMI 1640 supplemented with 10% inactivated FBS, 100 U/ml penicillin and streptomycin sulfate), and stimulated with anti-CD3 and anti-CD28mAb-coated beads (invitrogen). Twelve hours after activation, T cells were transduced with lentiviral vectors in presence of 4 μg/ml polybrene. Human T lymphocytes were expanded and maintained by addition of interleukin-2 every other day at 100 IU/ml.

$^{51}$Cr Release Assay

The ability of transduced T lymphocytes to lyse GPC3-positive tumor cells was evaluated using a $^{51}$Cr assay. Briefly, $10^6$ tumor cells were labeled for 1 h at 37 C with 100 μCi of 51Cr (Amersham Biosciences, Pittsburgh, Pa.). The labeled target cells ($1 \times 10^4$) were co-cultured with effector cells at the ratios indicated in the figures for 6 hours at 37 C in 150 μl of complete medium. Harvested supernatants were counted using a MicroBeta TriLux instrument (Perkin Elmer, Waltham, Mass.). Total and spontaneous 51Cr release was determined by incubating $1 \times 10^4$-labeled target cells in either 1% TRITON® X-100 or medium alone for the above conditions, respectively. Each data point was determined as the mean results from triplicate wells. Specific lysis was calculated by use of the following formula: % specific release=(cpm of exp−cpm of mean spontaneous)/(cpm of mean total−cpm of mean spontaneous).

Figure 8:
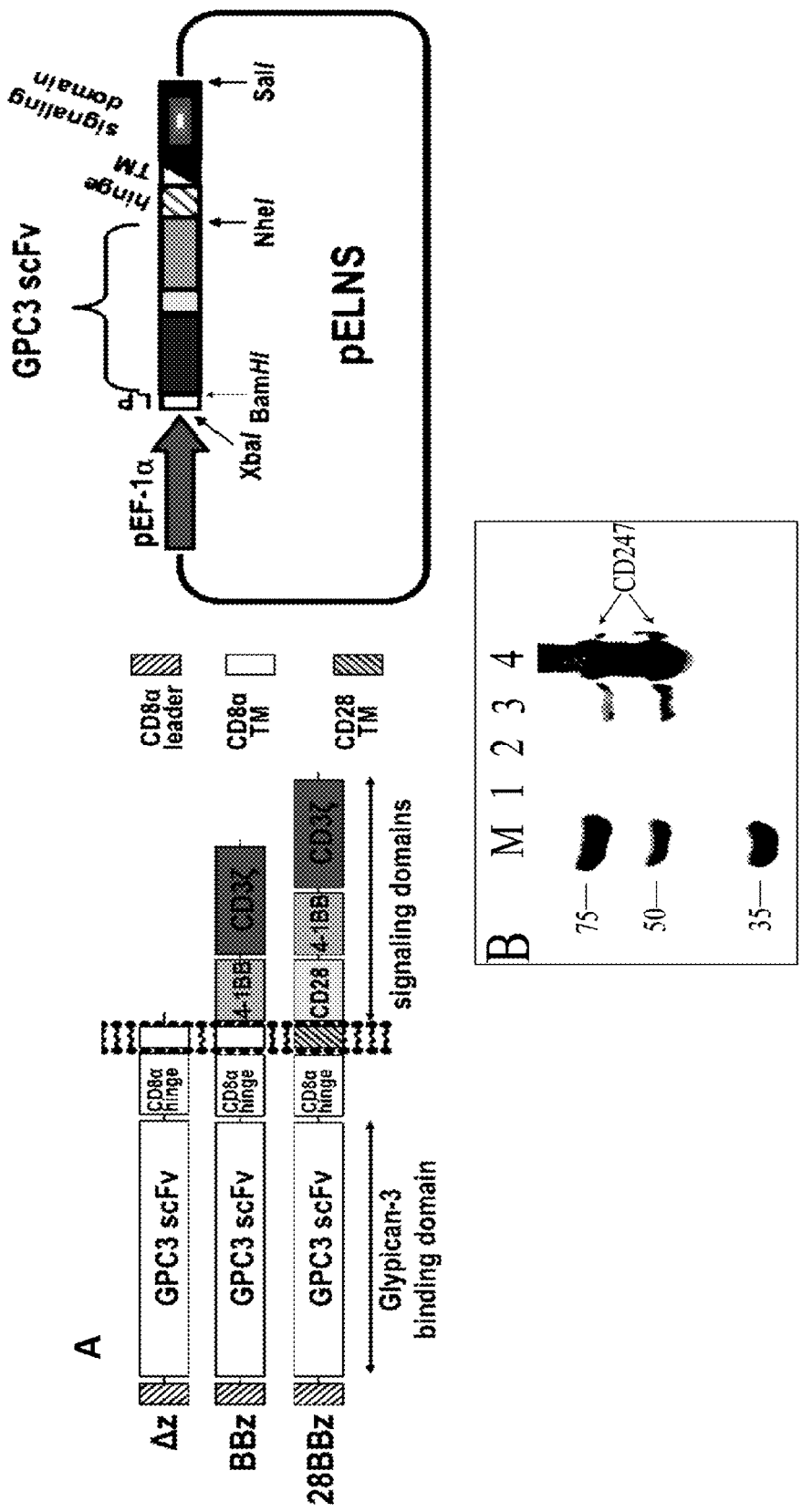
FIG. 8, comprising
Figure 8:
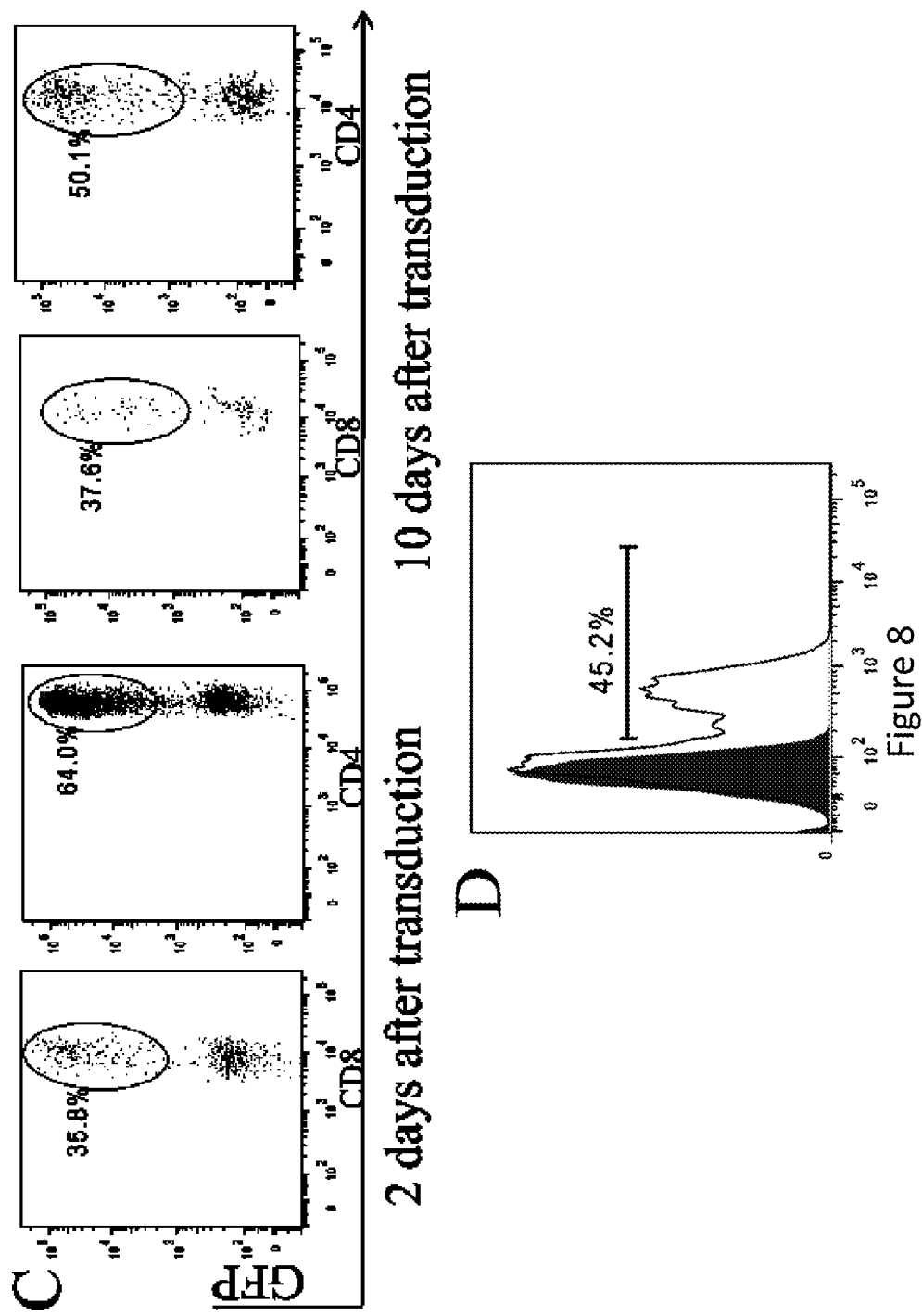

The results of the experiments are now described.
GPC3-Specific CAR Construction The 3E11 scFv was selected to construct GPC3-specific CAR for the reason of relative high antigen binding affinity among the identified scFvs. The lentiviral CAR-expressed vector presently used in the experiment has been optimized before (Carpenito, et al., 2009, Proc Natl Acad Sci USA 106:3360-3365) and constitute a CD8α hinge and transmembrane region, followed by a CD3 signaling moiety and in tandem with the CD137 (4-1BB) or CD28 intracellular signaling motif. A signaling deficient containing a truncated CD3 intracellular domain (Δξ) was designed as negative control to assess initiating signaling transduction as depicted in FIG. 8. The cDNA of scFv 3E11 was sub-cloned into these lentiviral-CAR vectors. Further, these vectors were transformed into 293T cells and western blot probed to CD3 confirmed successful expression by these vectors.

For effective lentiviral transduction, human T lymphocytes from peripheral blood were activated by CD3/CD28 beads. To test the transduction efficiency, T cells were transduced with GFP-expressed lentiviral vector, and the stable consistent GFP expression can be observed after 10 days transduction as depicted in FIG. 8. To track CAR expression on T cell membrane, one Flag-tag was artificially inserted on N-terminal of CAR, and the expression of CAR on T cell membrane was detected by FACS using anti-Flag mAb. The data as depicted in FIG. 8 suggested around 50% T cells were transduced and express CAR receptor on cell membranes.

3E11-CAR+ T Cells Showed GPC3-Specific Cytotoxicity In Vitro

Figure 9:
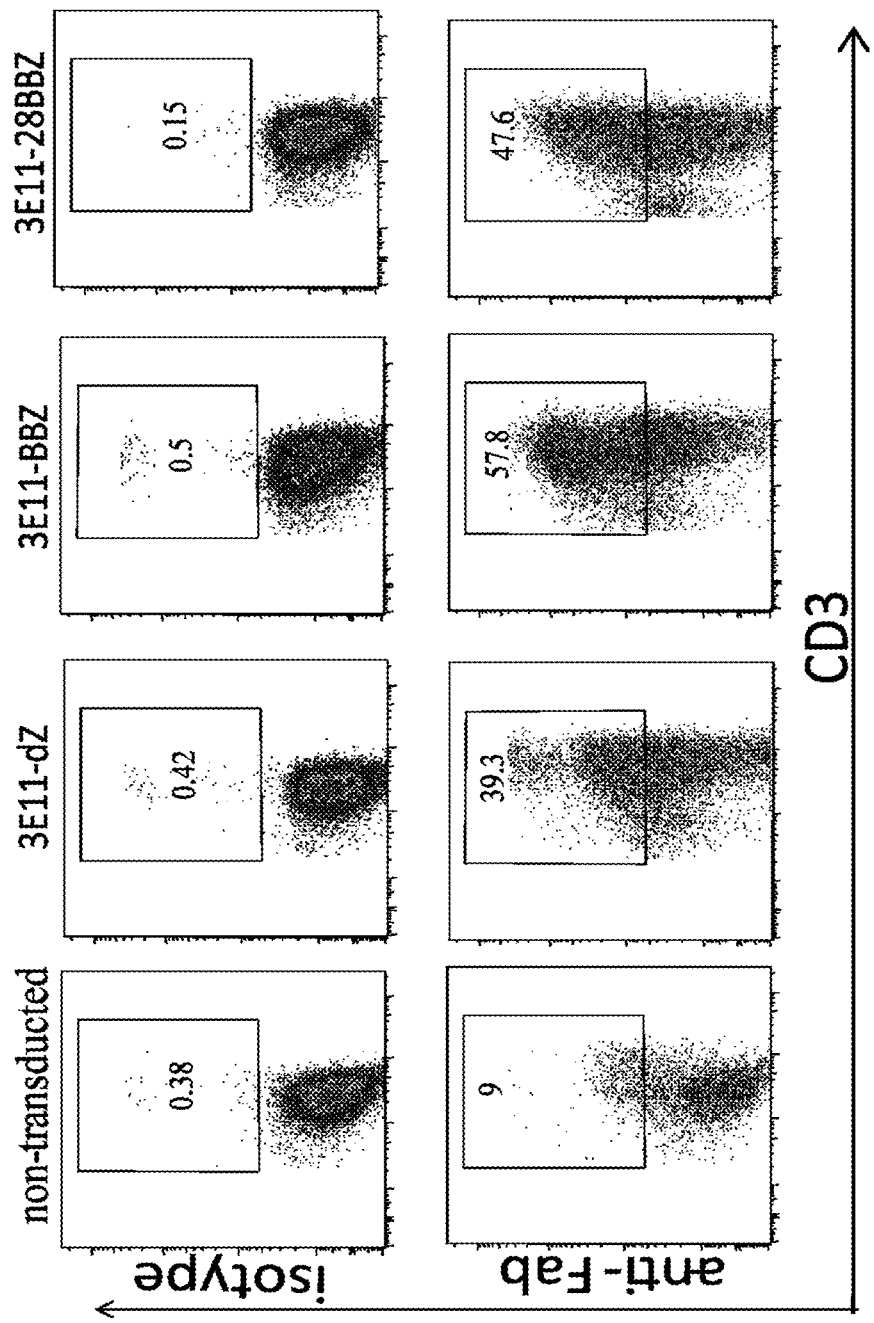
FIG. 9 is an image depicting results of 3E11-CAR expression on human T cells after transduction with lentivirus compared with parallel untransduced T cells. CD3+ T cells isolated from peripheral blood of healthy donor were placed in culture with anti-CD3/CD28 beads. The cells were transduced 1 day later with lentivirus encoding 3E11-dZ, and 3E11-BBZ, and 3E11-28BZ. The third day after culture initiation, the cells were analyzed for CAR expression by staining with anti-human Fab antibodies or isotype control antibodies. The activated but untransduced cells were used as control. Percent transduction is indicated.
Figure 10:
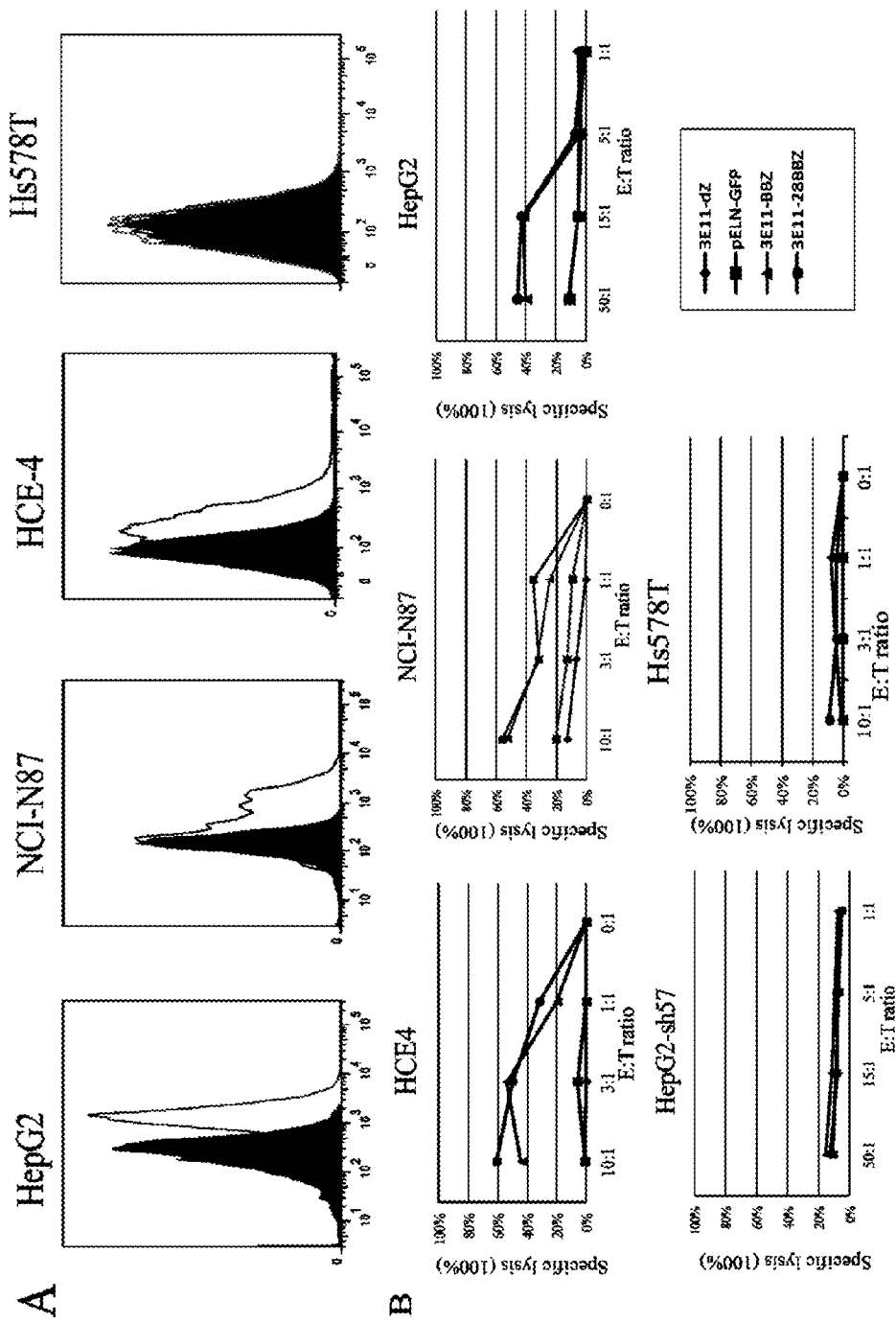
FIG. 10, comprising
Figure 11:
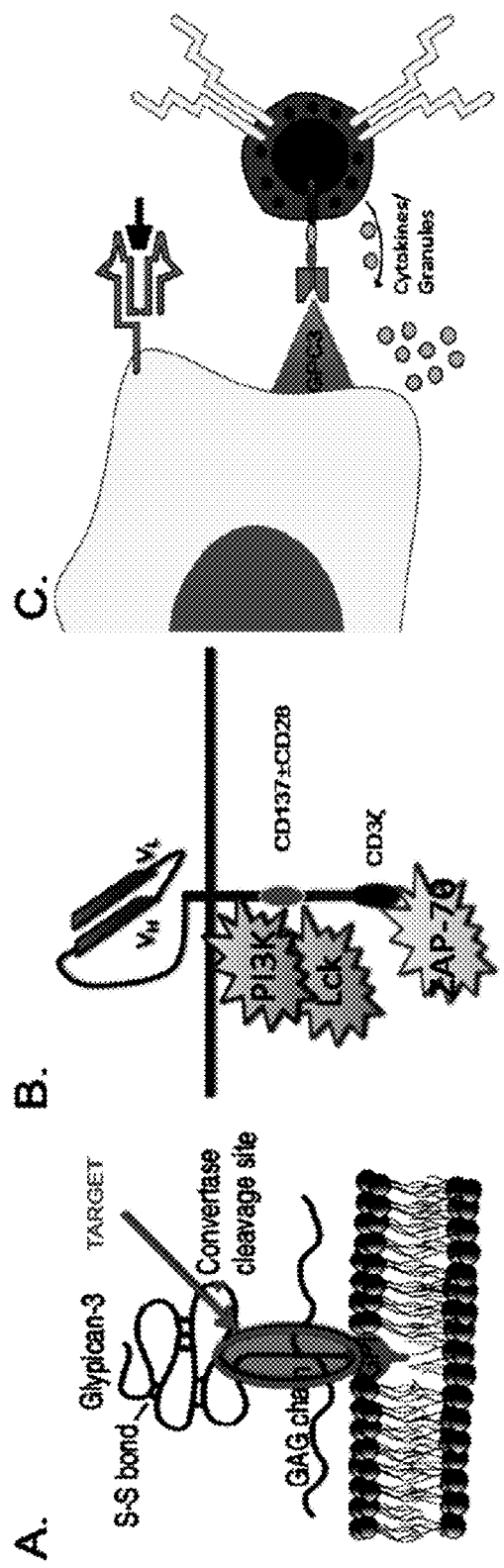
FIG. 11, comprising
Figure 12:
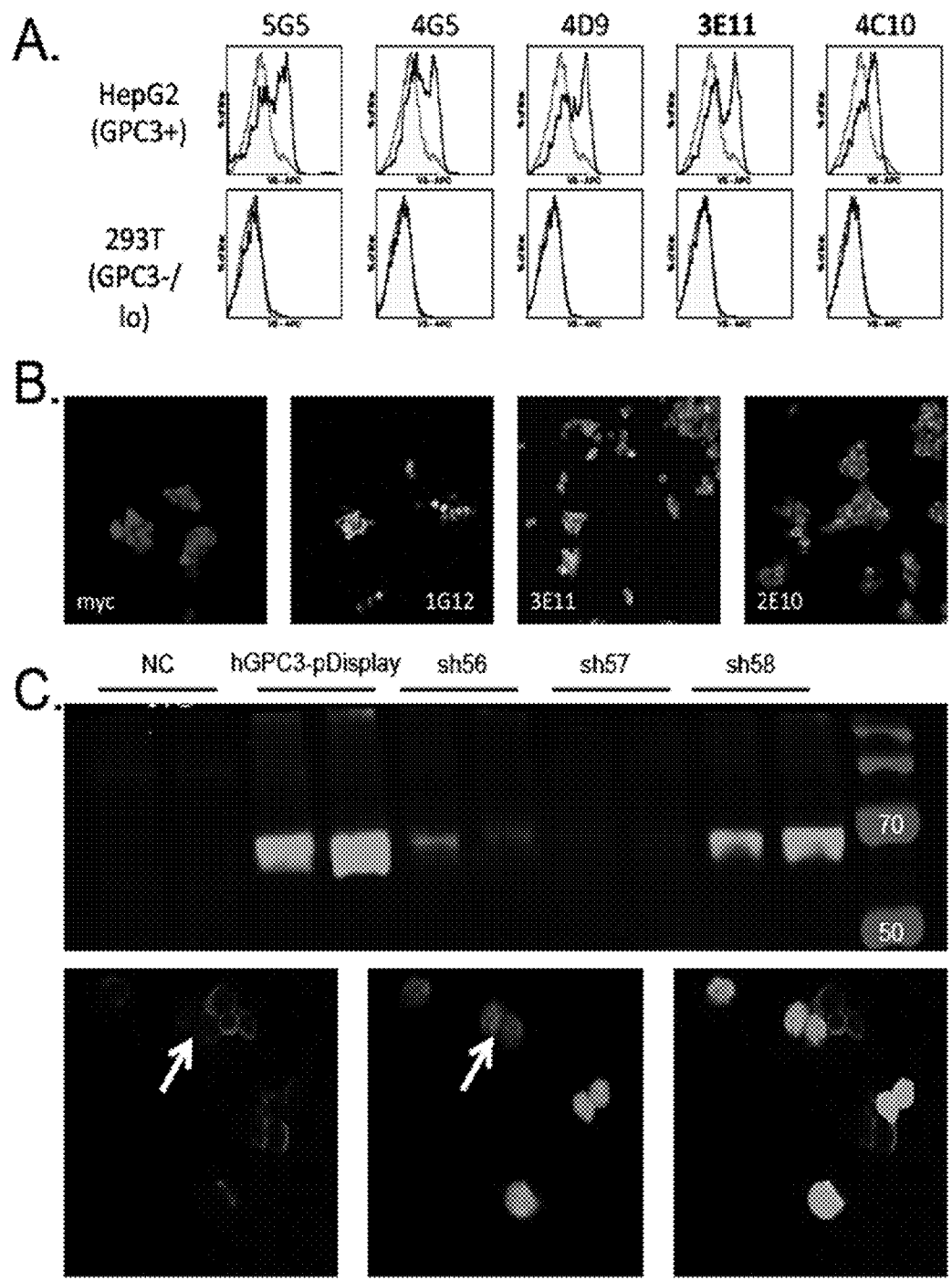
FIG. 12, comprising
Figure 12D:
Figure 13:
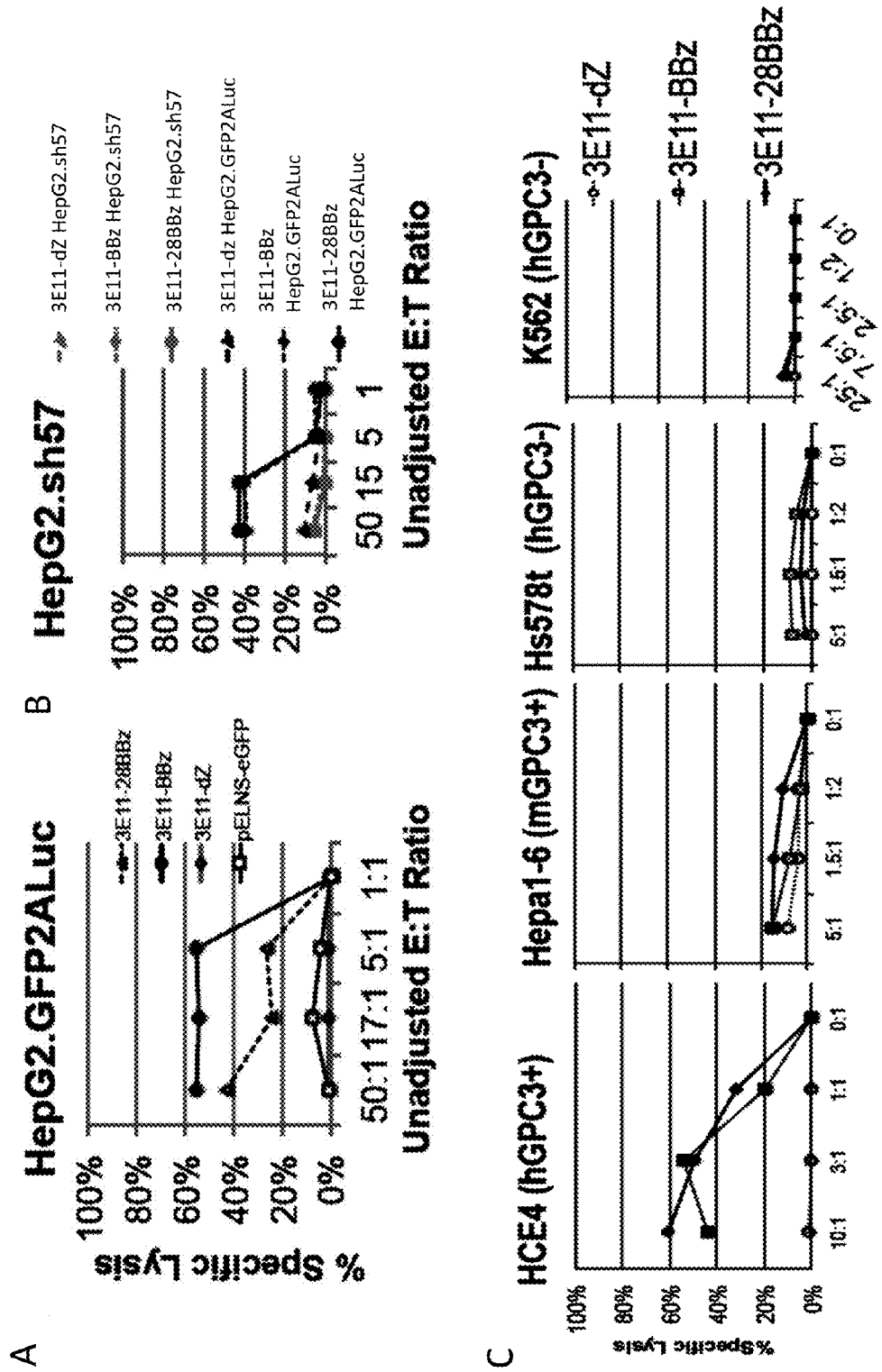
FIG. 13, comprising

Engineered T cells were cocultured with GPC3+ or GPC3-tumor cells to determine the effects of antigen specific cytotoxicity. T cells were transduced by lentiviral vector of 3E11-BBZ, 3E11-28BBZ, and 3E11-dZ, and their transduction efficiency were assessed by FACS, and further equilibrated to the similar cell numbers in the following cytotoxicity assays as depicted in FIG. 9. Also, T cells transduced with GFP lentiviral vector were included as control. For target cells, several established tumor cell lines were selected and GPC3 protein expression levels were determined by FACS. Two tumor cell lines, hs578T (GPC3−) and HepG2.sh57 (less GPC3 expression), were also selected. As shown in FIG. 10, T cells transduced with 3E11-BBZ or 3E11-28BBZ have significant cellular lysis of HepG2 ranged from 44-60% at E:T ratio of 5-15:1, while no lysis effects on 3E11-dZ and GFP transduced T cells. Similar lysis effects were observed on other two GPC3+ tumor cell lines of HCE4 and NCI-N87 cells. For Hs578T and HepG2.sh57 cells, no significant lysis was detected with 3E11-BBZ and 3E11-28BBZ transduced T cells. The present data suggested antigen-specific cytotoxicity by 3E11-CAR transduced T cells. The CAR transduced T cells can be used to target GPC3 expressing tumors as a type of T cell-based immunotherapy of HCC. The results presented herein provide a specific and human-sourced scFv for CAR-transduced T cells-based immunotherapy.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated and substantially purified polynucleotide encoding a single chain human anti-glypican-3 (GPC3) antibody fragment, wherein the single chain antibody fragment comprises a heavy chain variable region and light chain variable region, wherein the amino acid sequence of the heavy chain variable region and the amino acid sequence of the light chain variable region are selected from the group consisting of: (a) SEQ ID NO: 12 and SEQ ID NO: 17; (b) SEQ ID NO: 13 and SEQ ID NO: 18; (c) SEQ ID NO: 14 and SEQ ID NO: 19; and, (d) SEQ ID NO: 15 and SEQ ID NO: 20.

2. The isolated polynucleotide of claim 1, comprising nucleic acid sequences that encode the heavy chain variable region and light chain variable region, wherein the heavy chain variable region-encoding nucleic acid sequence and the light chain variable region-encoding nucleic acid sequence are selected from the group consisting of: (a) SEQ ID NO: 52 and SEQ ID NO: 57; (b) SEQ ID NO: 53 and SEQ ID NO: 58; (c) SEQ ID NO: 54 and SEQ ID NO: 59; and, (d) SEQ ID NO: 55 and SEQ ID NO: 60.

3. An isolated and substantially purified vector comprising the isolated polynucleotide of claim 1.

4. The vector of claim 3, wherein the vector is a viral vector selected from the group consisting of an adenoviral vector, an adeno-associated virus vector, a retroviral vector, a poxvirus, a herpes simplex virus I, and a lentiviral vector.

* * * * *

```
                         SEQUENCE LISTING

<160> NUMBER OF SEQ ID NOS: 63

<210> SEQ ID NO 1
<211> LENGTH: 21
<212> TYPE: DNA
<213> ORGANISM: Artificial
<220> FEATURE:
<223> OTHER INFORMATION: Chemically synthesized

<400> SEQUENCE: 1
atggccggga ccgtgcgcac c                                              21

<210> SEQ ID NO 2
<211> LENGTH: 24
<212> TYPE: DNA
<213> ORGANISM: Artificial
<220> FEATURE:
<223> OTHER INFORMATION: Chemically synthesized

<400> SEQUENCE: 2
tcagtgcacc aggaagaaga agca                                           24

<210> SEQ ID NO 3
<211> LENGTH: 35
<212> TYPE: DNA
<213> ORGANISM: Artificial
<220> FEATURE:
<223> OTHER INFORMATION: Chemically synthesized

<400> SEQUENCE: 3
ccggaattcg acaagaaagt attaaaagtt gctca                               35

<210> SEQ ID NO 4
<211> LENGTH: 32
<212> TYPE: DNA
<213> ORGANISM: Artificial
<220> FEATURE:
<223> OTHER INFORMATION: Chemically synthesized

<400> SEQUENCE: 4
acgcgtcgac ggtgcttatc tcgttgtcct tc                                  32

<210> SEQ ID NO 5
<211> LENGTH: 37
<212> TYPE: DNA
<213> ORGANISM: Artificial
<220> FEATURE:
<223> OTHER INFORMATION: Chemically synthesized

<400> SEQUENCE: 5
ggttctggtg gtggaggttc tggtggtggt ggatctg                             37
```

<210> SEQ ID NO 6
<211> LENGTH: 62
<212> TYPE: DNA
<213> ORGANISM: Artificial
<220> FEATURE:
<223> OTHER INFORMATION: Chemically synthesized

<400> SEQUENCE: 6
gagaccgagg agagggttag ggataggctt accgtcgacc aagtcttctt cagaataagc    60
tt    62

<210> SEQ ID NO 7
<211> LENGTH: 21
<212> TYPE: DNA
<213> ORGANISM: Artificial
<220> FEATURE:
<223> OTHER INFORMATION: Chemically synthesized

<400> SEQUENCE: 7
gccaaattat tctcctatgt t    21

<210> SEQ ID NO 8
<211> LENGTH: 21
<212> TYPE: DNA
<213> ORGANISM: Artificial
<220> FEATURE:
<223> OTHER INFORMATION: Chemically synthesized

<400> SEQUENCE: 8
gccaatatag atctgcttat t    21

<210> SEQ ID NO 9
<211> LENGTH: 21
<212> TYPE: DNA
<213> ORGANISM: Artificial
<220> FEATURE:
<223> OTHER INFORMATION: Chemically synthesized

<400> SEQUENCE: 9
gctcaagaaa gatggaagaa a    21

<210> SEQ ID NO 10
<211> LENGTH: 28
<212> TYPE: DNA
<213> ORGANISM: Artificial
<220> FEATURE:
<223> OTHER INFORMATION: Chemically synthesized

<400> SEQUENCE: 10
ggatccgtcc agtctgtgtt gacgcagc    28

<210> SEQ ID NO 11
<211> LENGTH: 29
<212> TYPE: DNA
<213> ORGANISM: Artificial
<220> FEATURE:
<223> OTHER INFORMATION: Chemically synthesized

<400> SEQUENCE: 11
gctagctgag gagacggtga ccagtgttc    29

<210> SEQ ID NO 12
<211> LENGTH: 117
<212> TYPE: PRT

```
<213> ORGANISM: Artificial
<220> FEATURE:
<223> OTHER INFORMATION: Chemically synthesized

<400> SEQUENCE: 12

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Leu His Trp Val Arg Gln Ala Pro Gly Lys Gly Leu Glu Trp Val
        35                  40                  45

Ala Ala Ile Ser Tyr Asp Gly Ser Lys Lys Tyr Tyr Ala Asp Ser Val
50                  55                  60

Lys Gly Arg Leu Thr Ile Ser Arg Asp Asn Ser Lys Asn Thr Leu Tyr
65                  70                  75                  80

Leu Gln Met Asn Ser Leu Ser Pro Glu Asp Thr Ala Leu Tyr Phe Cys
                85                  90                  95

Ala Arg Gly Trp Phe Val Glu Pro Leu Ser Trp Gly Gln Gly Thr Leu
            100                 105                 110

Val Thr Val Ser Ser
        115

<210> SEQ ID NO 13
<211> LENGTH: 124
<212> TYPE: PRT
<213> ORGANISM: Artificial
<220> FEATURE:
<223> OTHER INFORMATION: Chemically synthesized

<400> SEQUENCE: 13

Gln Val Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Ser Ser Ser
            20                  25                  30

Ser Tyr Tyr Trp Ala Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Phe Pro Leu Ile Arg Gly Tyr Arg Tyr Arg Tyr Asp Glu
            100                 105                 110

Tyr Trp Gly Gln Gly Thr Leu Val Thr Val Ser Ser
        115                 120

<210> SEQ ID NO 14
<211> LENGTH: 123
<212> TYPE: PRT
<213> ORGANISM: Artificial
<220> FEATURE:
<223> OTHER INFORMATION: Chemically synthesized

<400> SEQUENCE: 14

Gln Val Gln Leu Gln Glu Ser Gly Leu Gly Leu Val Lys Pro Ser Glu
1               5                   10                  15

Thr Leu Ser Leu Thr Cys Ala Val Ser Gly Tyr Ser Ile Thr Ser Gly
            20                  25                  30
```

```
Tyr Tyr Trp Gly Trp Ile Arg Gln Thr Pro Gly Lys Gly Leu Glu Trp
            35                  40                  45

Ile Gly Arg Ile Tyr Tyr Gly Gly Ser Thr His Tyr Asn Pro Ser Leu
 50                  55                  60

Gln Ser Arg Val Thr Ile Ser Val Asp Thr Ala Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Arg Asn Tyr Gln Ser Leu Ser Gly Tyr Cys Leu Asp Tyr
                100                 105                 110

Trp Gly Gln Gly Lys Val Val Thr Val Ser Ser
            115                 120
```

```
<210> SEQ ID NO 15
<211> LENGTH: 118
<212> TYPE: PRT
<213> ORGANISM: Artificial
<220> FEATURE:
<223> OTHER INFORMATION: Chemically synthesized

<400> SEQUENCE: 15
```

```
Gln Val Gln Leu Val Gln Ser Gly Gly Gly Leu Ala Gln Pro Gly Gly
 1               5                  10                  15

Ser Leu Arg Leu Ser Cys Ala Ala Ser Gly Ser Ser Phe Ser Thr Phe
                 20                  25                  30

Val Leu Ser Trp Val Arg Gln Thr Pro Gly Lys Gly Leu Gln Trp Val
            35                  40                  45

Ser Thr Ile Ser Gly Ser Gly Thr Ser Thr Tyr Tyr Ala Asp Ser Val
 50                  55                  60

Lys Gly Arg Phe Thr Val Ser Arg Asp Asn Ala Lys Asn Thr Gln Tyr
 65                  70                  75                  80

Leu Gln Met Asn Ser Leu Arg Ala Glu Asp Thr Ala Ile Tyr Tyr Cys
                 85                  90                  95

Ala Arg His Lys Ser Phe Gly Val Gln Trp Leu Trp Gly Gln Gly Ala
                100                 105                 110

Leu Val Val Arg Leu Leu
            115
```

```
<210> SEQ ID NO 16
<211> LENGTH: 127
<212> TYPE: PRT
<213> ORGANISM: Artificial
<220> FEATURE:
<223> OTHER INFORMATION: Chemically synthesized

<400> SEQUENCE: 16
```

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
```

```
            85                  90                  95
Cys Ala Arg Val His Asp Gly His Arg Tyr Gly Thr Tyr Tyr Tyr Tyr
                100                 105                 110
Gly Leu Asp Val Trp Gly Gln Gly Thr Ala Val Thr Val Ser Ser
            115                 120                 125
```

<210> SEQ ID NO 17
<211> LENGTH: 109
<212> TYPE: PRT
<213> ORGANISM: Artificial
<220> FEATURE:
<223> OTHER INFORMATION: Chemically synthesized

<400> SEQUENCE: 17

```
Ser Val Leu Thr Gln Pro Pro Ser Ala Ser Gly Thr Pro Gly Gln Arg
1               5                   10                  15
Val Thr Ile Ser Cys Ser Gly Ser Ser Ser Asn Ile Gly Ser Asn Thr
            20                  25                  30
Val Asn Trp Tyr Gln Gln Leu Pro Gly Thr Ala Pro Lys Leu Leu Ile
        35                  40                  45
Tyr Ser Asn Asn Gln Arg Pro Ser Gly Val Pro Asp Arg Phe Ser Gly
50                  55                  60
Ser Lys Ser Gly Thr Ser Ala Ser Leu Ala Ile Ser Gly Leu Gln Ser
65                  70                  75                  80
Glu Asp Glu Ala Asp Tyr Tyr Cys Ala Ala Trp Asp Asp Ser Leu Asn
                85                  90                  95
Gly Tyr Val Phe Gly Thr Gly Thr Lys Leu Thr Val Leu
                100                 105
```

<210> SEQ ID NO 18
<211> LENGTH: 114
<212> TYPE: PRT
<213> ORGANISM: Artificial
<220> FEATURE:
<223> OTHER INFORMATION: Chemically synthesized

<400> SEQUENCE: 18

```
Val Asp Ile Val Met Thr Gln Ser Pro Leu Ser Leu Pro Val Thr Pro
1               5                   10                  15
Gly Glu Ala Ala Ser Ile Ser Cys Arg Ser Ser Gln Ser Leu Leu His
            20                  25                  30
Arg Asp Gly Tyr His Tyr Leu Asn Trp Phe Leu Gln Lys Pro Gly Gln
        35                  40                  45
Ser Pro Gln Leu Leu Ile Tyr Leu Gly Ser Asn Arg Ala Ser Gly Val
50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Ala Pro Gln Thr Pro Arg Thr Leu Leu Gly Gln Gly Thr Lys Leu Glu
                100                 105                 110
Ile Lys
```

<210> SEQ ID NO 19
<211> LENGTH: 110
<212> TYPE: PRT
<213> ORGANISM: Artificial
<220> FEATURE:
<223> OTHER INFORMATION: Chemically synthesized

<400> SEQUENCE: 19

Val Glu Ile Val Leu Thr Gln Ser Pro Gly Thr Leu Ser Val Ser Pro
1               5                   10                  15

Gly Glu Arg Ala Thr Leu Ser Cys Arg Ala Ser Gln Ser Val Ser Ser
                20                  25                  30

His Ile Ala Trp Tyr Gln Gln Lys Pro Gly Gln Ala Pro Arg Leu Leu
            35                  40                  45

Ile His Gly Ala Ser Thr Arg Ala Thr Gly Val Pro Ala Arg Phe Ser
        50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Lys Trp Pro
                85                  90                  95

Pro Glu Tyr Thr Phe Gly Gln Gly Thr Lys Leu Glu Ile Lys
            100                 105                 110

<210> SEQ ID NO 20
<211> LENGTH: 114
<212> TYPE: PRT
<213> ORGANISM: Artificial
<220> FEATURE:
<223> OTHER INFORMATION: Chemically synthesized

<400> SEQUENCE: 20

Val His Ile Val Met Thr Gln Ser Pro Leu Ser Leu Pro Val Thr Leu
1               5                   10                  15

Gly Gln Pro Ala Ser Ile Ser Cys Trp Ser Ser Gln Ser Leu Val Tyr
                20                  25                  30

Gly Asp Gly Asn Thr Tyr Leu Asn Trp Phe Gln Gln Arg Pro Gly Gln
            35                  40                  45

Ser Pro Arg Arg Leu Ile Tyr Lys Val Ser Asn Arg Asp Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Trp Pro Pro Gly Thr Phe Gly Gly Gly Thr Lys Leu Glu
            100                 105                 110

Ile Lys

<210> SEQ ID NO 21
<211> LENGTH: 108
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (16)..(16)
<223> OTHER INFORMATION: Xaa can be any naturally occurring amino acid

<400> SEQUENCE: 21

Asp Ile Val Met Thr Gln Ser Pro Leu Ser Leu Pro Val Thr Pro Xaa
1               5                   10                  15

Glu Ala Ala Ser Ile Ser Cys Arg Ser Ser Gln Ser Leu Tyr Ser Ala
                20                  25                  30

Trp Glu Thr Leu Leu Glu Leu Leu Gln Gln Ile Lys Pro Ile Ser Lys
            35                  40                  45

```
Gly Ala Thr Tyr Lys Val Ser Asn Arg Asp Ser Gly Val Gln Thr Asp
        50                  55                  60

Gln Arg Gln Trp Val Arg His Trp Phe His Thr Glu Asn Gln Gln Val
65                  70                  75                  80

Glu Ala Glu Asp Val Gly Val Ile Thr Ala Cys Lys Val His Thr Gly
                85                  90                  95

Pro Pro Phe Ser Ala Pro Gly Pro Lys Trp Ile Ser
            100                 105

<210> SEQ ID NO 22
<211> LENGTH: 5
<212> TYPE: PRT
<213> ORGANISM: Artificial
<220> FEATURE:
<223> OTHER INFORMATION: Chemically synthesized

<400> SEQUENCE: 22

Ser Tyr Gly Leu His
1               5

<210> SEQ ID NO 23
<211> LENGTH: 17
<212> TYPE: PRT
<213> ORGANISM: Artificial
<220> FEATURE:
<223> OTHER INFORMATION: Chemically synthesized

<400> SEQUENCE: 23

Ala Ile Ser Tyr Asp Gly Ser Lys Lys Tyr Tyr Ala Asp Ser Val Lys
1               5                   10                  15

Gly

<210> SEQ ID NO 24
<211> LENGTH: 8
<212> TYPE: PRT
<213> ORGANISM: Artificial
<220> FEATURE:
<223> OTHER INFORMATION: Chemically synthesized

<400> SEQUENCE: 24

Gly Trp Phe Val Glu Pro Leu Ser
1               5

<210> SEQ ID NO 25
<211> LENGTH: 7
<212> TYPE: PRT
<213> ORGANISM: Artificial
<220> FEATURE:
<223> OTHER INFORMATION: Chemically synthesized

<400> SEQUENCE: 25

Ser Ser Ser Tyr Tyr Trp Ala
1               5

<210> SEQ ID NO 26
<211> LENGTH: 16
<212> TYPE: PRT
<213> ORGANISM: Artificial
<220> FEATURE:
<223> OTHER INFORMATION: Chemically synthesized

<400> SEQUENCE: 26

Asn Ile Tyr Tyr Ser Gly Ser Thr Tyr Tyr Asn Pro Ser Leu Lys Ser
1               5                   10                  15
```

```
<210> SEQ ID NO 27
<211> LENGTH: 14
<212> TYPE: PRT
<213> ORGANISM: Artificial
<220> FEATURE:
<223> OTHER INFORMATION: Chemically synthesized

<400> SEQUENCE: 27

Phe Pro Leu Ile Arg Gly Tyr Arg Tyr Arg Tyr Asp Glu Tyr
1               5                   10

<210> SEQ ID NO 28
<211> LENGTH: 6
<212> TYPE: PRT
<213> ORGANISM: Artificial
<220> FEATURE:
<223> OTHER INFORMATION: Chemically synthesized

<400> SEQUENCE: 28

Ser Gly Tyr Tyr Trp Gly
1               5

<210> SEQ ID NO 29
<211> LENGTH: 16
<212> TYPE: PRT
<213> ORGANISM: Artificial
<220> FEATURE:
<223> OTHER INFORMATION: Chemically synthesized

<400> SEQUENCE: 29

Arg Ile Tyr Tyr Gly Gly Ser Thr His Tyr Asn Pro Ser Leu Gln Ser
1               5                   10                  15

<210> SEQ ID NO 30
<211> LENGTH: 14
<212> TYPE: PRT
<213> ORGANISM: Artificial
<220> FEATURE:
<223> OTHER INFORMATION: Chemically synthesized

<400> SEQUENCE: 30

Asp Arg Asn Tyr Gln Ser Leu Ser Gly Tyr Cys Leu Asp Tyr
1               5                   10

<210> SEQ ID NO 31
<211> LENGTH: 5
<212> TYPE: PRT
<213> ORGANISM: Artificial
<220> FEATURE:
<223> OTHER INFORMATION: Chemically synthesized

<400> SEQUENCE: 31

Ser Tyr Ala Met Ser
1               5

<210> SEQ ID NO 32
<211> LENGTH: 17
<212> TYPE: PRT
<213> ORGANISM: Artificial
<220> FEATURE:
<223> OTHER INFORMATION: Chemically synthesized

<400> SEQUENCE: 32

Ala Ile Ser Gly Ser Gly Thr Ser Thr Tyr Tyr Ala Asp Ser Val Lys
1               5                   10                  15
```

Gly

<210> SEQ ID NO 33
<211> LENGTH: 9
<212> TYPE: PRT
<213> ORGANISM: Artificial
<220> FEATURE:
<223> OTHER INFORMATION: Chemically synthesized

<400> SEQUENCE: 33

His Lys Ser Phe Gly Val Gln Trp Leu
1               5

<210> SEQ ID NO 34
<211> LENGTH: 7
<212> TYPE: PRT
<213> ORGANISM: Artificial
<220> FEATURE:
<223> OTHER INFORMATION: Chemically synthesized

<400> SEQUENCE: 34

Ser Ser Ser Tyr Tyr Trp Gly
1               5

<210> SEQ ID NO 35
<211> LENGTH: 16
<212> TYPE: PRT
<213> ORGANISM: Artificial
<220> FEATURE:
<223> OTHER INFORMATION: Chemically synthesized

<400> SEQUENCE: 35

Ser Ile Tyr Tyr Ser Gly Ser Thr Tyr Tyr Asn Pro Ser Leu Lys Ser
1               5                   10                  15

<210> SEQ ID NO 36
<211> LENGTH: 14
<212> TYPE: PRT
<213> ORGANISM: Artificial
<220> FEATURE:
<223> OTHER INFORMATION: Chemically synthesized

<400> SEQUENCE: 36

His Asp Gly His Arg Tyr Gly Thr Tyr Tyr Gly Leu Asp Val
1               5                   10

<210> SEQ ID NO 37
<211> LENGTH: 13
<212> TYPE: PRT
<213> ORGANISM: Artificial
<220> FEATURE:
<223> OTHER INFORMATION: Chemically synthesized

<400> SEQUENCE: 37

Ser Gly Ser Ser Ser Asn Ile Gly Ser Asn Thr Val Asn
1               5                   10

<210> SEQ ID NO 38
<211> LENGTH: 7
<212> TYPE: PRT
<213> ORGANISM: Artificial
<220> FEATURE:
<223> OTHER INFORMATION: Chemically synthesized

<400> SEQUENCE: 38

Ser Asn Asn Gln Arg Pro Ser
1               5

<210> SEQ ID NO 39
<211> LENGTH: 8
<212> TYPE: PRT
<213> ORGANISM: Artificial
<220> FEATURE:
<223> OTHER INFORMATION: Chemically synthesized

<400> SEQUENCE: 39

Gly Trp Phe Val Glu Pro Leu Ser
1               5

<210> SEQ ID NO 40
<211> LENGTH: 16
<212> TYPE: PRT
<213> ORGANISM: Artificial
<220> FEATURE:
<223> OTHER INFORMATION: Chemically synthesized

<400> SEQUENCE: 40

Arg Ser Ser Gln Ser Leu Leu His Arg Asp Gly Tyr His Tyr Leu Asn
1               5                   10                  15

<210> SEQ ID NO 41
<211> LENGTH: 7
<212> TYPE: PRT
<213> ORGANISM: Artificial
<220> FEATURE:
<223> OTHER INFORMATION: Chemically synthesized

<400> SEQUENCE: 41

Leu Gly Ser Asn Arg Ala Ser
1               5

<210> SEQ ID NO 42
<211> LENGTH: 8
<212> TYPE: PRT
<213> ORGANISM: Artificial
<220> FEATURE:
<223> OTHER INFORMATION: Chemically synthesized

<400> SEQUENCE: 42

Met Gln Ala Pro Gln Thr Pro Arg
1               5

<210> SEQ ID NO 43
<211> LENGTH: 11
<212> TYPE: PRT
<213> ORGANISM: Artificial
<220> FEATURE:
<223> OTHER INFORMATION: Chemically synthesized

<400> SEQUENCE: 43

Arg Ala Ser Gln Ser Val Ser Ser His Ile Ala
1               5                   10

<210> SEQ ID NO 44
<211> LENGTH: 7
<212> TYPE: PRT
<213> ORGANISM: Artificial
<220> FEATURE:
<223> OTHER INFORMATION: Chemically synthesized

<400> SEQUENCE: 44

Gly Ala Ser Thr Arg Ala Thr
1               5

```
<210> SEQ ID NO 45
<211> LENGTH: 7
<212> TYPE: PRT
<213> ORGANISM: Artificial
<220> FEATURE:
<223> OTHER INFORMATION: Chemically synthesized

<400> SEQUENCE: 45

Gln Gln Tyr Asn Lys Trp Pro
1               5

<210> SEQ ID NO 46
<211> LENGTH: 16
<212> TYPE: PRT
<213> ORGANISM: Artificial
<220> FEATURE:
<223> OTHER INFORMATION: Chemically synthesized

<400> SEQUENCE: 46

Trp Ser Ser Gln Ser Leu Val Tyr Gly Asp Gly Asn Thr Tyr Leu Asn
1               5                   10                  15

<210> SEQ ID NO 47
<211> LENGTH: 7
<212> TYPE: PRT
<213> ORGANISM: Artificial
<220> FEATURE:
<223> OTHER INFORMATION: Chemically synthesized

<400> SEQUENCE: 47

Lys Val Ser Asn Arg Asp Ser
1               5

<210> SEQ ID NO 48
<211> LENGTH: 9
<212> TYPE: PRT
<213> ORGANISM: Artificial
<220> FEATURE:
<223> OTHER INFORMATION: Chemically synthesized

<400> SEQUENCE: 48

Met Gln Gly Thr His Trp Pro Pro Gly
1               5

<210> SEQ ID NO 49
<211> LENGTH: 15
<212> TYPE: PRT
<213> ORGANISM: Artificial
<220> FEATURE:
<223> OTHER INFORMATION: Chemically synthesized

<400> SEQUENCE: 49

Ser Ser Gln Ser Leu Val Tyr Ser Asp Gly Asn Thr Tyr Leu Asn
1               5                   10                  15

<210> SEQ ID NO 50
<211> LENGTH: 7
<212> TYPE: PRT
<213> ORGANISM: Artificial
<220> FEATURE:
<223> OTHER INFORMATION: Chemically synthesized

<400> SEQUENCE: 50

Lys Val Ser Asn Arg Asp Ser
1               5
```

<210> SEQ ID NO 51
<211> LENGTH: 8
<212> TYPE: PRT
<213> ORGANISM: Artificial
<220> FEATURE:
<223> OTHER INFORMATION: Chemically synthesized

<400> SEQUENCE: 51

Met Gln Gly Thr His Trp Pro Pro
1               5

<210> SEQ ID NO 52
<211> LENGTH: 349
<212> TYPE: DNA
<213> ORGANISM: Artificial
<220> FEATURE:
<223> OTHER INFORMATION: Chemically synthesized

<400> SEQUENCE: 52

```
caggtgcagc tggtgcagtc tggggggaggc gtggtccagc ctgggaggtc cctgagactc      60
tcctgtgcag cctctggatt caccttcagt agctatggct tgcactgggt ccgccaggct     120
ccaggcaagg gctggagtg gtggcagct atatcatatg atggtagtaa gaaatactat       180
gcagactccg tgaagggccg actcaccatc tccagagaca attccaagaa cacgctgtat    240
ctgcaaatga acagtttgag acctgacgac acggctctgt atttctgtgc gaggggatgg    300
ttcgtggagc cactatcctg gggccaggaa cactggtcac gtctcctca                349
```

<210> SEQ ID NO 53
<211> LENGTH: 373
<212> TYPE: DNA
<213> ORGANISM: Artificial
<220> FEATURE:
<223> OTHER INFORMATION: Chemically synthesized

<400> SEQUENCE: 53

```
caggtgcagc tgcaggagtc gggcccagga ctggtgaagc cttcggagac cctgtccctc      60
agctgcactg tctctggtgg ctccatcagc agtagtagtt actactgggc ctggatccgc     120
cagcccccag ggaaggggct ggagtggatt ggcaatatct actatagtgg gagcacctac     180
tacaacccgt ccctcaagag tcgagtcacc atatcagtag acacgtccaa gaaccagttc     240
tccctgaagc tgagctctgt gaccgccgcg gacacggccg tgtattactg tgcgagattc     300
cctttaatac gtggatacag atatcgttac gatgagtact ggggccaggg aacgctggtc     360
accgtctcct cag                                                       373
```

<210> SEQ ID NO 54
<211> LENGTH: 369
<212> TYPE: DNA
<213> ORGANISM: Artificial
<220> FEATURE:
<223> OTHER INFORMATION: Chemically synthesized

<400> SEQUENCE: 54

```
caggtgcagc tgcaggagtc gggcctagga ctggtgaagc cttcggagac cctgtccctc      60
acatgcgctg tctctggtta ctccatcacc agtggttact actggggctg gatccggcag     120
acgccaggga aggactgga gtggattgga cgtatctatt atggtgggag cacccactac      180
aacccatccc tccagagtcg agtcaccata tcagtagaca cggccaagaa tcagttctcc    240
ctgaagctga gctctgtgac cgccgcagac acggccgtct attactgtgc gagagaccgg    300
aattaccaga gtttgagcgg ttattgctta gactactggg gccagggaaa ggtggtcacc   360
```

```
<210> SEQ ID NO 55
<211> LENGTH: 356
<212> TYPE: DNA
<213> ORGANISM: Artificial
<220> FEATURE:
<223> OTHER INFORMATION: Chemically synthesized

<400> SEQUENCE: 55
caggtgcagc tggtgcagtc tgggggaggc ttggcacagc ctgggggtc cctgagactc      60 tcctgtgcag cctctggatc cagcttcagc accttcgtct taagttgggt ccgccagact     120
ccagggaagg ggctgcaatg ggtctcaact attagtggta gtggtactag cacatactac     180
gcagactccg tgaagggccg attcaccgtc tccagagaca tgccaagaa cacacagtat      240 ttgcaaatga acagcttgag agccgaggac acggccatat attactgtgc gagacacaaa    300
tctttcgggg ttcagtggct gtggggccag ggagcgctgg tcgtccgtct cctcag         356

<210> SEQ ID NO 56
<211> LENGTH: 382
<212> TYPE: DNA
<213> ORGANISM: Artificial
<220> FEATURE:
<223> OTHER INFORMATION: Chemically synthesized

<400> SEQUENCE: 56
caggtgcagc tgcaggagtc gggcccagga ctggtcaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagctctgt gaccgccgca gacacggctg tgtattactg tgcgagagtt    300
catgacggac acaggtatgg tacctactac tactacggtc tagacgtctg gggccaaggg   360
accgcggtca ccgtctcctc ag                                               382

<210> SEQ ID NO 57
<211> LENGTH: 336
<212> TYPE: DNA
<213> ORGANISM: Artificial
<220> FEATURE:
<223> OTHER INFORMATION: Chemically synthesized

<400> SEQUENCE: 57
gtccagtctg tgttgacgca gccgccctca gcgtctggga ccccgggca gagggtcacc      60 atctcttgtt ctggaagcag ctccaacatc ggaagtaata ctgtaaactg gtaccagcag    120
ctcccaggaa cggcccccaa actcctcatc tatagtaata tcagcggcc ctcaggggtc     180 cctgaccgat tctctggctc caagtctggc acctcagcct ccctggccat cagtgggctc    240
cagtctgagg atgaggctga ttattactgt gcagcatggg atgacagcct gaatgggtat   300
gtcttcggaa ctggcaccaa gctgaccgtc ctaggc                               336

<210> SEQ ID NO 58
<211> LENGTH: 342
<212> TYPE: DNA
<213> ORGANISM: Artificial
<220> FEATURE:
<223> OTHER INFORMATION: Chemically synthesized
```

<400> SEQUENCE: 58

```
gtcgatattg tgatgactca gtctccactc tccctgcccg tcaccctgg agaggcggcc      60
tccatctcct gcaggtctag tcagagcctc ctgcatagag atggatacca ctatttgaat    120
tggttcctgc agaagccagg gcagtctcca cagctcctga tctatttggg ttctaatcgg    180
gcctccgggg tccctgacag gttcagtggc agtggatcag gcacagattt tacactgaaa    240
atcagcagag tggaggctga ggatgttggg gtgtattact gcatgcaagc tccacagact    300
cctaggacac ttttgggcca ggggaccaag ctggagatca aa                       342
```

<210> SEQ ID NO 59
<211> LENGTH: 330
<212> TYPE: DNA
<213> ORGANISM: Artificial
<220> FEATURE:
<223> OTHER INFORMATION: Chemically synthesized

<400> SEQUENCE: 59

```
gtcgaaattg tgttgacgca gtctccaggc accctgtctg tgtctccagg ggaaagagcc      60
accctctcct gcagggccag tcagagtgtt agcagccaca tagcctggta ccagcagaaa    120
cctggccagg ctcctaggct cctcatccat ggtgcatcca ccagggccac tggtgtccca    180
gccaggttca gtggcagcgg gtctgggaca gagttcactc tcaccatcag cagcttgcag    240
tctgaagatt ttgcagtttta ttactgtcag cagtataata gtggcctcc agagtacact    300
tttggccagg ggaccaagct ggagatcaaa                                     330
```

<210> SEQ ID NO 60
<211> LENGTH: 342
<212> TYPE: DNA
<213> ORGANISM: Artificial
<220> FEATURE:
<223> OTHER INFORMATION: Chemically synthesized

<400> SEQUENCE: 60

```
gtccatattg tgatgaccca gtctccactc tccctgcccg tcacccttgg acagccggcc      60
tccatctcct gctggtctag tcaaagcctc gtatacggtg atggaaacac ctacttgaat    120
tggtttcagc agaggccagg ccaatctcca aggcgcctaa tttataaggt ttctaaccgg    180
gactctgggg tcccagacag attcagcggc agtgggtcag gcactgattt cacactgaaa    240
atcagcaggg tggaggctga ggatgttggg gtttattact gcatgcaagg tacacactgg    300
cctccgggta ctttcggcgg agggaccaag ctggagatca aa                       342
```

<210> SEQ ID NO 61
<211> LENGTH: 380
<212> TYPE: DNA
<213> ORGANISM: Artificial
<220> FEATURE:
<223> OTHER INFORMATION: Chemically synthesized

<400> SEQUENCE: 61

```
gatattgtga tgactcagtc tccactctcc ctgcccgtca ccctgrrga ggcggcctcc      60
atctcctgca ggtctagtca gagcctctac agtgcatggg aaacactact tgaattgctt    120
cagcagatca agccaatctc caaaggcgct acttataaag tttctaaccg cgactctggg    180
gtccagacag atcagcggca gtgggtcagg cactggtttc acactgaaaa tcagcaggtg    240
gaggctgagg atgttggggt tattactgca tgcaaggtac acactggccc ccgttttcg    300
gccccgggac caaagtggat atcaaaggtg gttcctctag atcttcctcc tctggtggcg    360
```

```
gtggctcggg cggtggtggg                                                   380

<210> SEQ ID NO 62
<211> LENGTH: 26
<212> TYPE: DNA
<213> ORGANISM: Artificial
<220> FEATURE:
<223> OTHER INFORMATION: Chemically synthesized

<400> SEQUENCE: 62
cccggggcca cctgtcacca agtccg                                             26

<210> SEQ ID NO 63
<211> LENGTH: 28
<212> TYPE: DNA
<213> ORGANISM: Artificial
<220> FEATURE:
<223> OTHER INFORMATION: Chemically synthesized

<400> SEQUENCE: 63
ccgcgggtgc accaggaaga agaagcac                                           28
```